United States Patent
Leburton

(10) Patent No.: US 10,677,752 B2
(45) Date of Patent: Jun. 9, 2020

(54) METHOD AND APPARATUS ANALYZING A TARGET MATERIAL

(71) Applicants: Jean-Pierre Leburton, Urbana, IL (US); THE BOARD OF TRUSTEES OF THE UNIVERSITY OF ILLINOIS, Urbana, IL (US)

(72) Inventor: Jean-Pierre Leburton, Urbana, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 403 days.

(21) Appl. No.: 14/781,106

(22) PCT Filed: Oct. 4, 2013

(86) PCT No.: PCT/US2013/063379
§ 371 (c)(1),
(2) Date: Sep. 29, 2015

(87) PCT Pub. No.: WO2014/171969
PCT Pub. Date: Oct. 23, 2014

(65) Prior Publication Data
US 2016/0054260 A1    Feb. 25, 2016

Related U.S. Application Data

(60) Provisional application No. 61/813,220, filed on Apr. 18, 2013.

(51) Int. Cl.
*G01N 27/447* (2006.01)
*G01N 27/453* (2006.01)
(Continued)

(52) U.S. Cl.
CPC ......... *G01N 27/447* (2013.01); *C12Q 1/6869* (2013.01); *G01N 27/453* (2013.01); *G01N 33/48721* (2013.01)

(58) Field of Classification Search
CPC .............. G01N 27/447; G01N 27/453; G01N 33/48721; C12Q 2565/631; C12Q 1/6869
See application file for complete search history.

(56) References Cited

U.S. PATENT DOCUMENTS

| 8,713,607 B2 | 4/2014 | McEnroe et al. |
| 2004/0055875 A1 | 3/2004 | Siwy et al. |

(Continued)

FOREIGN PATENT DOCUMENTS

| WO | 2012/138357 | 10/2012 |
| WO | 2013/016486 | 1/2013 |

OTHER PUBLICATIONS

Branton et al, the potential and challenges of nanopore sequencing, 2008, Nature biotechnology, vol. 26, No. 10, pp. 1146-1153.*

(Continued)

*Primary Examiner* — Bethany L Martin
(74) *Attorney, Agent, or Firm* — Guntin & Gust, PLC; Mark Wilinski

(57) ABSTRACT

Aspects of the subject disclosure may include, for example, an apparatus including a material having one or more atomic layers with two or less degrees of freedom for motion of charges in the material, and a gate coupled to the material for controlling charge concentration of the material. The material can have constricted sides, a first through-hole, and a first port and a second port for conduction of charges in the material. The gate can have a second through-hole that is at least partially aligned with the first through-hole. A first voltage potential can be applied to the first port and the second port, along with a second voltage potential applied to the gate which adjusts the charge concentration of the material. A sensor can be used to measure a change in electrical properties of the material caused by a target (Continued)

material traversing the first through-hole of the material. Additional embodiments are disclosed.

23 Claims, 15 Drawing Sheets

(51) Int. Cl.
  *G01N 33/487* (2006.01)
  *C12Q 1/6869* (2018.01)

(56) References Cited

U.S. PATENT DOCUMENTS

| | | | |
|---|---|---|---|
| 2008/0187915 A1 | 8/2008 | Polonsky et al. | |
| 2008/0192820 A1 | 8/2008 | Brooks et al. | |
| 2010/0327847 A1 | 12/2010 | Leiber et al. | |
| 2013/0176563 A1* | 7/2013 | Ozawa | B82Y 5/00 356/301 |
| 2014/0174927 A1* | 6/2014 | Bashir | C12Q 1/6827 204/452 |
| 2014/0190833 A1* | 7/2014 | Lieber | B82Y 30/00 204/627 |
| 2015/0028846 A1 | 1/2015 | Zhu | |
| 2016/0187290 A1 | 6/2016 | Leburton | |

OTHER PUBLICATIONS

Ozyilmaz et al, Electronic transport in locally gated graphene nanoconstrictions, 2007, Applied Physics Letters, vol. 91 pp. 192107-1 through 192107-3.*

Branton, Daniel et al., "The potential and challenges of nanopore sequencing", Nature Biotechnology, 26(10), pp. 1146-1153, Oct. 2008.
Dekker, Cees, "Solid-state nanopores", Kavli Institute of Nanoscience, 2007.
Girdhar, A. et al., "Graphene quantum point contact transistor for DNA sensing", PNAS—Proceedings of the National Academy of Sciences, vol. 110, No. 42, Sep. 30, 2013, 16748-16753.
Gracheva, et al., "Simulation of the Electric Response of DNA Translocation Through a Semiconductor Nanopore-Capacitor", Nanotechnology, 2006, 622-633.
Humphrey, William et al., "VMD: Visual Molecular Dynamics", J. of Molecular Graphics, 1996, 33-38.
Li, Jiali et al., "DNA Molecules and Configurations in a Solid-State Nanopore Microscope", Nat. Mater, 2003, 611-615.
Mali, P. et al., "The dnaSET: a novel device for single-molecule DNA sequencing", IEEE Transactions on Electron Devices, vol. 51, No. 12, 2004.
Ozyilmaz, et al., "Electronic transport in locally gated graphene nanoconstrictions", Applied Physics Letters, vol. 91, No. 19, 2007.
Stampfer, C. et al., "Tunable graphene single electron transistor", NANO Letters, vol. 8, No. 8, 2008.
Storm, et al., "Fabrication of Solid-State nanopores with Single-Nanometre Precision", Nat. Mater., 2003, 537-540.
Rycerz, A. et al., "Valley Filter and Valley Valve in Graphene", Nature Physics, vol. 3, p. 172-175, Mar. 2007, 172-175.
Venkatesan, Bala Murali, et al. "Stacked graphene-Al2O3 nanopore sensors for sensitive detection of DNA and DNA protein complexes." ACS nano 6.1 (2011): 441-450.†
Postma, Henk W. Ch. "Rapid sequencing of individual DNA molecules in graphene nanogaps." Nano letters 10.2 (2010): 420-425.†

* cited by examiner
† cited by third party

METHOD AND APPARATUS ANALYZING A TARGET MATERIAL

PRIOR APPLICATIONS

The present application claims the benefit of priority to PCT Application Serial No. PCT/US13/63379, filed Oct. 4, 2013, which claims priority to U.S. Provisional Application No. 61/813,220 filed on Apr. 18, 2013, the disclosures of which are hereby incorporated by reference in their entirety.

FIELD OF THE DISCLOSURE

The subject disclosure relates generally to a method and apparatus for analyzing a target material.

BACKGROUND

Sequencing of biological materials such as, deoxyribonucleic acid, also known as DNA, is expected to become a vital means for diagnosing and in some instances predicting susceptibility to disease. The cost of instrumentation and the speed of sequencing by such instrumentation is an important driver for the availability of this technology to the general public. Improvements and innovation of instrumentation of this kind is therefore desirable. It is also expected that such instruments can also be used for analyzing other forms of biological and non-biological materials.

BRIEF DESCRIPTION OF THE DRAWINGS

Reference will now be made to the accompanying drawings, which are not necessarily drawn to scale, and wherein.

DETAILED DESCRIPTION

Figure 1:
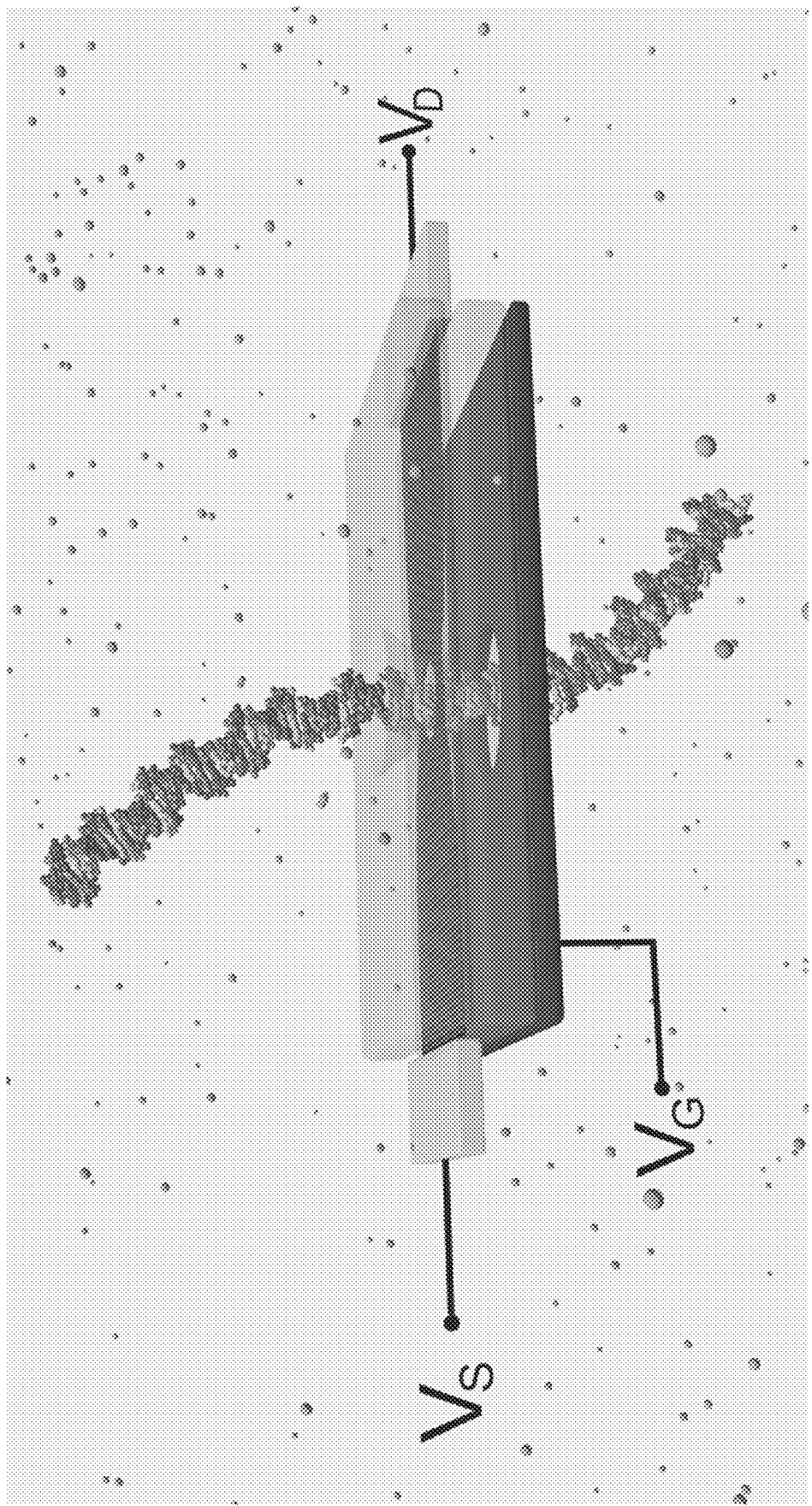
FIG. 1: Schematic diagram of a prototypical solid-state, multilayer device containing a GNR layer (black) with a nanopore, sandwiched between two oxides (transparent) atop a heavily doped Si back-gate, $V_G$ (green). The DNA is translocated through the pore, and the current is measured with the source and drain leads, $V_S$ and $V_D$ (gold). (See FIG. 12 for a cross-sectional schematic diagram).

One embodiment of the subject disclosure entails a method for providing a material having one or more atomic layers with two or less degrees of freedom for motion of charges in the material, constricting the material to generate a constriction in the material to configure electrical properties in the material, coupling a first end of the material to a first electrode, coupling a second end of the material to a second electrode, coupling a gate to the material, providing a first through-hole in the material near a vicinity of the constriction, providing a second through-hole in the gate, wherein the first through-hole and the second through-hole are substantially coaxially aligned, introducing a target material at one of the first through-hole or the second through-hole to analyze the target material, applying a first voltage potential to the first electrode and the second electrode to the material, applying a second voltage potential to the gate to adjust a charge concentration of the material, and measuring a change in electrical properties of the material responsive to the target material traversing the first through-hole of the material.

One embodiment of the subject disclosure entails an apparatus including a material having one or more atomic layers with two or less degrees of freedom for motion of charges in the material, and a gate coupled to the material for controlling charge concentration of the material. The material can have constricted sides, a first through-hole, and a first port and a second port for conduction of charges in the material. The gate can have a second through-hole that is at least partially aligned with the first through-hole. A first voltage potential can be applied to the first port and the second port, along with a second voltage potential applied to the gate which adjusts the charge concentration of the material. A sensor can be used to measure a change in electrical properties of the material caused by a target material traversing the first through-hole of the material.

One embodiment of the subject disclosure entails an apparatus including a material having one or more atomic layers with two or less degrees of freedom for motion of charges in the material, wherein the material comprises constricted sides and a first through-hole, a gate coupled to the material for controlling charge concentration of the material, wherein the gate comprises a second through-hole, a sensor, and a controller coupled to the material, the gate and the sensor. The controller can perform operations comprising applying a first voltage potential to the material, applying a second voltage potential to the gate to adjust a charge concentration of the material, and receiving sensing data from the sensor responsive to a change in electrical properties of the material caused by a target traversing the first through-hole of the material.

Over the past few years the need has grown for low-cost, high-speed, and accurate biomolecule sensing, propelling the so-called third generation of genome sequencing devices. Many associated technologies have been developed, but recent advances in the fabrication of solid-state nanopores have shown that the translocation of biomolecules such as DNA through such pores is a promising alternative to traditional sensing methods. Some of these methods include measuring (1) ionic blockade current fluctuations through nanopores in the presence of nucleotides, (2) tunneling-currents across nanopores containing biomolecules, and (3) direct transverse-current measurements. Graphene is a candidate for such measurements. Studies suggest that functionalized graphene nanopores can be used to differentiate passing ions, demonstrating the potential use of graphene membranes in nanofluidics and molecular sensing. In addition, its atomic-scale thickness allows a molecule passing through it to be scanned at the highest possible resolution, and the feasibility of using graphene nanopores for DNA detection has been demonstrated experimentally. Lastly, electrically-active graphene can, in principle, both control and probe translocating molecules, acting as a gate as well as a charge sensor which passive, oxide-based nanopore devices are incapable of doing.

Molecular dynamics studies describing the electrophoresis of DNA translocation through graphene nanopores demonstrated that DNA sequencing by measuring ionic current blockades is possible in principle. Additionally, several groups have reported first-principles-based studies to identify base-pairs using tunneling currents or transverse conductance-based approaches. Saha et al. (see Saha K, Drndić M, Nikolić B (2011) DNA base-specific modulation of microampere transverse edge currents through a metallic graphene nanoribbon with a nanopore. *Nano Lett* 12(1):50-55) reported transverse edge current variations of the order of 1 µA through graphene nanoribbons (GNR) caused by the presence of isolated nucleotides in a nanopore and reported base-pair specific edge currents. These studies, however, do not account for solvent or screening effects; the latter effects are due to the presence of ions in the solution and can reduce the ability of the nanoribbon to discern individual nucleotides. Very recently, Avdoshenko et al. (see Avdoshenko S, Nozaki D, Gomes da Rocha C, Gonzalez J, Lee M et al. (2013) Dynamic and electronic transport properties of DNA translocation through graphene nanopores. *Nano Lett* 13(5): 1969-1976) investigated the influence of single-stranded DNA on sheet currents in GNRs with nanopores. However, their study does not consider the carrier concentration modulation of the current, the influence of the GNR-edge boundary-condition on the nanopore sensitivity, or a self-consistent treatment of screening due to charged ions in solution.

GNRs are strips of graphene with a finite width that quantizes the energy states of the conduction electrons. Unlike traditional quantum wells, the boundary conditions of GNRs are complicated functions of position and momentum resulting from the dual sublattice symmetry of graphene, giving rise to a unique band structure. Because of this, the shape of the boundary as well as the presence of nanopores profoundly affects the electronic states of GNRs, for example, leading to a difference in band structure for zigzag and armchair-edged GNRs.

The edge of a GNR can be patterned with near-atomic precision, opening up the possibility to investigate different geometries. In the case of complicated edge shapes, the current displays an extremely nonlinear and not strictly increasing dependence on carrier concentration. The graphene Quantum Point Contact (g-QPC) is an example in this regard, as its irregular edge yields a complex band structure and rich conductance spectrum with many regions of high sensitivity and negative differential transconductance (NDTC) as shown below. In addition, the g-QPC electronic properties are not limited by stringent GNR uniformity (armchair or zigzag) in the boundary conditions. Moreover, the carrier concentration itself, which can be controlled by the presence of a back-gate embedded within a g-QPC device, can affect the sensitivity and nonlinearity of the current. As a result, changes in external electric fields, including changes due to rotation and translation of external molecular charges, alter the local carrier concentration and can influence the g-QPC conductance.

The subject disclosure demonstrates complex and nonlinear effects of altering boundary shapes, graphene carrier concentrations, and electric potentials due to DNA translocation on the conductance of such a device. The subject disclosure presents illustrative embodiments for sensing DNA by performing transport measurements in a g-QPC device and demonstrating that the sensitivity of the conductance can be geometrically and electronically tuned to detect small differences in the charge geometry of biomolecules such as DNA.

FIG. 1 shows a monolayer g-QPC device in an ionic water solution, containing a single layer of patterned graphene connected to source and drain leads and sandwiched between two oxide layers to isolate the graphene from the aqueous environment. The graphene and oxide layers have coaxial nanopores ranging from 2 to 4 nm, allowing charges, molecules, or polymers to pass through. An aspect of the device shown is a back gate underneath the lower oxide substrate made of a metal or heavily-doped semiconductor or another graphene layer to control the charge carrier concentration in graphene (the gate layer could in practice be capped by an oxide layer to avoid unwanted electrochemistry); the back-gate enhances its electrical sensitivity to DNA translocation. The diameter of the nanopore is small enough to attain the required sensitivity, but is wide enough to let the biomolecules translocate.

Figure 2:
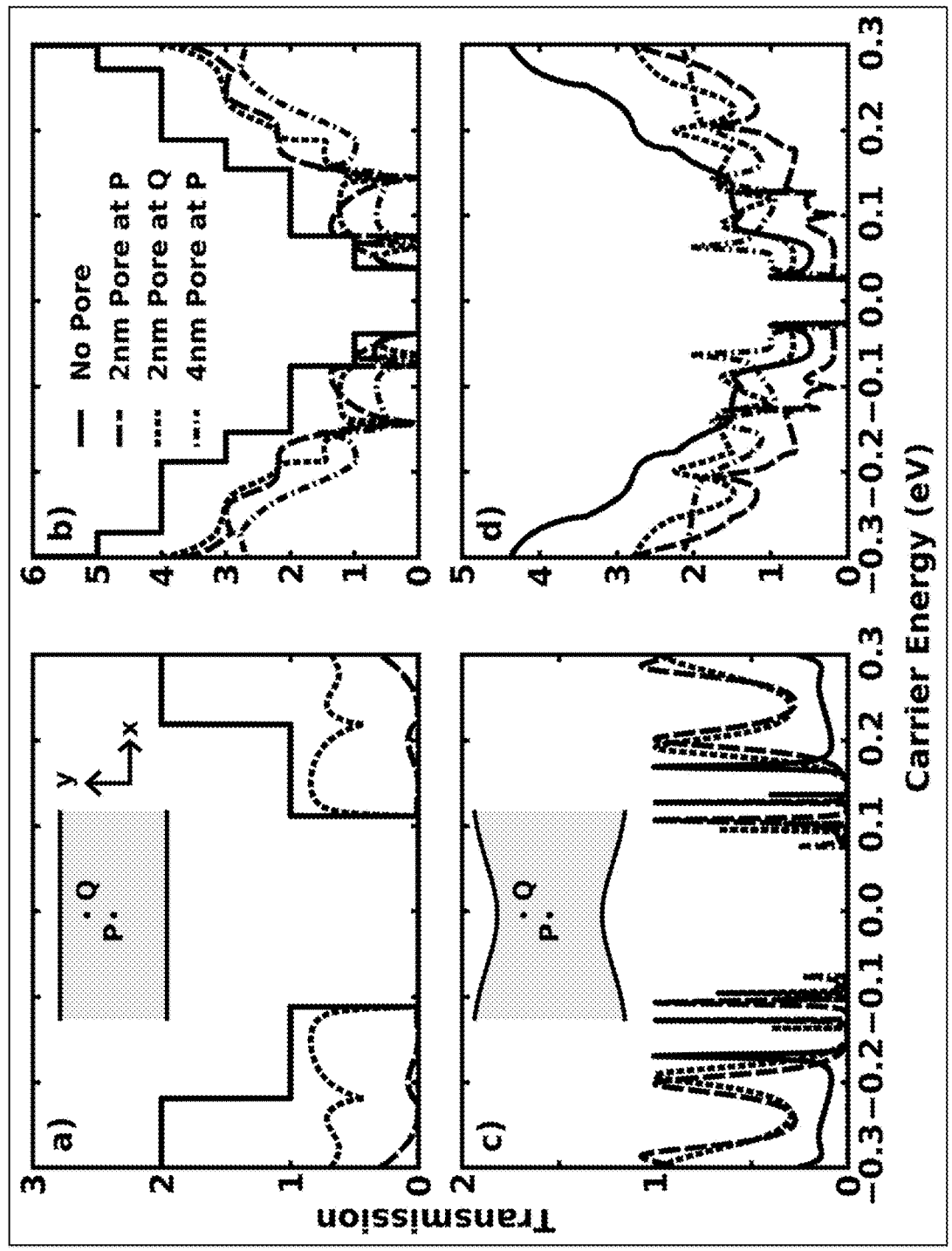
FIG. 2: Transmission functions for various edge geometries and pore configurations: a) 5 nm (5-GNR) and b) 15 nm (15-GNR) wide GNR-edged devices, c) 8 nm (8-QPC) and d) 23 nm (23-QPC) wide QPC-edged devices. Pristine (solid), a 2 nm pore at point P (long dash), a 2 nm pore at point Q (short dash), and a 4 nm pore at point P (dot dash).

The subject disclosure presents four edge geometries, namely a 5 nm wide (FIG. 2a) and a 15 nm wide (FIG. 2b) pure armchair-edge GNR (FIG. 2a inset) as well as an 8 nm wide (FIG. 2c) and a 23 nm wide (FIG. 2d) QPC edge (FIG. 2c inset). These geometries will herein be referred to as 5-GNR, 15-GNR, 8-QPC, and 23-QPC. The QPC geometries have pinch widths of 5 nm and 15 nm (⅔ total width), the same as the widths of the armchair-edged GNRs. For each edge geometry, four pore configurations are considered: pristine (no pore), a 2 nm pore in the center (point P in FIG. 2), a 2 nm pore centered at 75% of the total (pinch) width for the GNR (QPC) (point Q in FIG. 2), and a 4 nm pore at the center (point P in FIG. 2).

FIG. 2 demonstrates the effects of the different edge geometries and pore configurations previously described on the transmission spectra for suspended graphene nanoribbons in vacuum. A Fermi energy range is chosen from 0 to or smaller than 0.5 eV, which corresponds to carrier concentrations varying from $\sim 10^{11}$ cm$^{-2}$ to $5$-$7 \times 10^{12}$ cm$^{-2}$ at a temperature of 300 K, easily achievable in a conventional g-FET. The transmission for the pristine (no pore) 5-GNR edge exhibits the classic staircase shape resulting from the armchair-edge boundary conditions (FIG. 2a). The presence of a nanopore introduces a scatterer in the GNR, which manifests itself as additional boundary conditions at the pore edge, restricting the transmission in two ways: first, the number of allowed electronic states becomes reduced due to the need of satisfying more stringent boundary conditions; second, the electronic states that do satisfy these boundary conditions generally have smaller probability currents due to scattering off the nanopore. The resulting transmission probability varies largely within narrow carrier energy ranges and exhibits resonances at particular carrier energies, revealing the strong dependence of transmission probability on carrier energy. Increasing the pore diameter enhances the scattering nature of the nanopore, thereby reducing the transmission probability, as can be seen in FIG. 2a, where the 5-GNR with a 4 nm pore has an almost negligible transmission probability for most carrier energies in the represented range. By changing the nanopore positions, the particular wavelengths of the electronic states that satisfy the boundary conditions vary, which further affects the transmission probability. For instance, the transmission of the GNR with the pore at Q is higher at lower energies compared to the GNR with the pore at P, since the allowed electronic states at these lower energies have larger wavelengths.

Similar trends can be seen for the transmission probability determined for the 15-GNR (FIG. 2b). Because of the larger width compared to that of 5-GNR, there are significantly more electronic states within a particular carrier energy range, increasing the transmission probability for all pore configurations. This results in more closely-spaced transmission steps in the pristine GNR. As for 5-GNR with and without pore, pore edge boundary conditions destroy the stair-case behavior of the transmission seen for pristine 15-GNR as well as reduce the magnitude of the transmission probability. In contrast, because of the larger width, the density of allowed electronic states in the 15-GNR is larger at high energies compared to the respective density in the 5-GNR. As a result, both pore configurations P and Q in the 15-GNR have a similar number of allowed electronic states within a specific energy range, minimizing the difference in transmission between the two configurations at higher carrier energies.

FIG. 2c shows the transmission probability for the 8-QPC which exhibits strong variations as compared to that in the 5 or 15-GNR, because the non-uniform QPC edge introduces more stringent boundary conditions on the electronic states, especially when the QPC contains a nanopore. The transmission probability curves for the pristine 8-QPC and for the 8-QPC with a pore exhibit many resonance peaks throughout the Fermi energy range. It can be seen that the 4 nm pore (green curve) exhibits negligible transmission probability over the whole Fermi energy range, except around the band gap, which is reflected in two resonance peaks in both the conduction and valence bands. Increasing the width in going from the 8- to 23-QPC increases the density of states within an energy range, smoothing out the transmission at higher carrier energies as in the case of the 15-GNR (FIG. 2d). The influence of the position and size of the nanopore on the transmission function follows the same trend as with the 15-GNR at high carrier energies as mentioned above.

Figure 3:
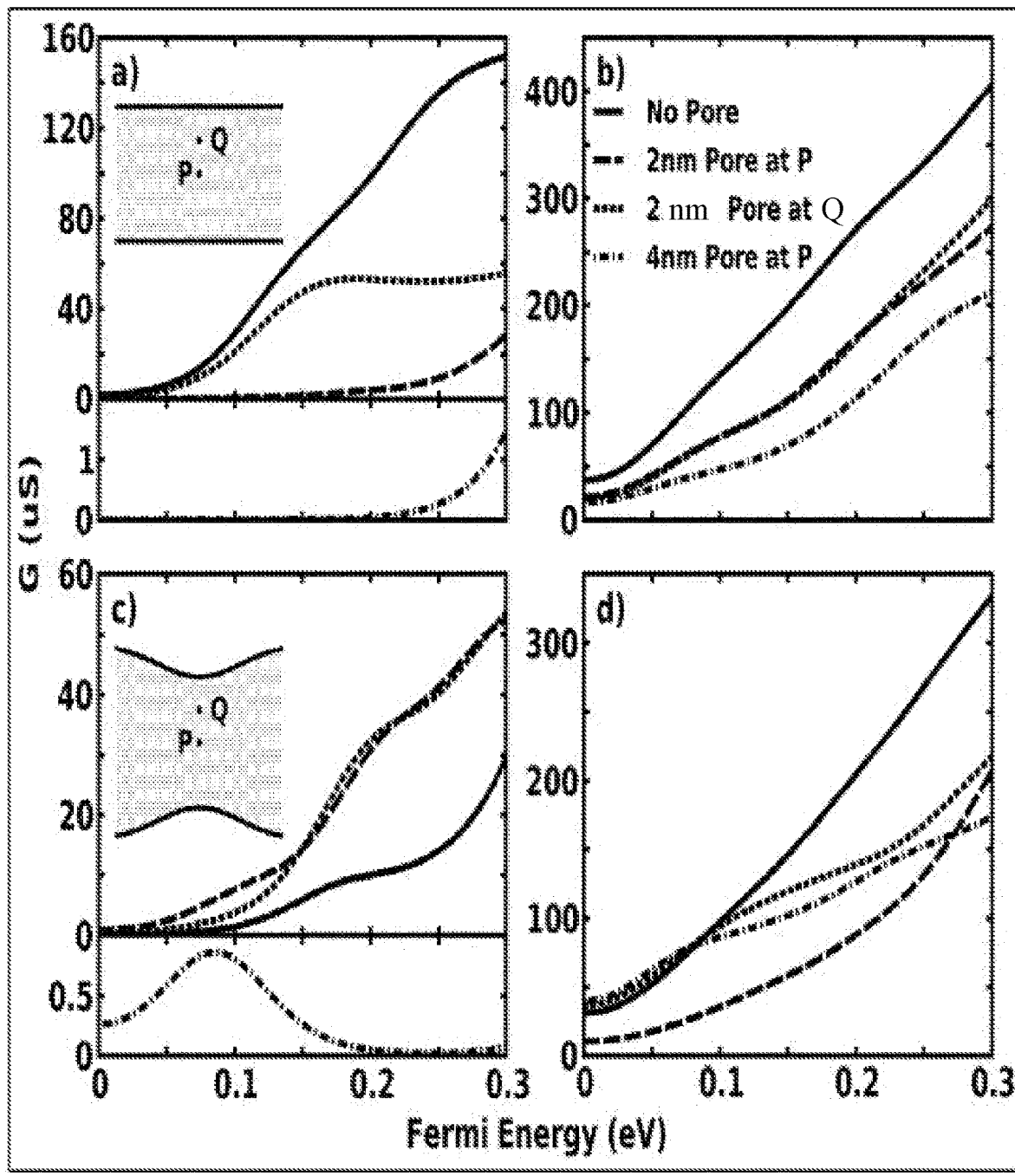
FIG. 3: Conductance versus Fermi energy (as a function of carrier concentration) for the four edge geometries with four pore configurations for each geometry. a) 5-GNR, b) 15-GNR, c) 8-QPC and d) 23-QPC. Pristine (solid), 2 nm pore at point P (long dash), 2 nm pore at point Q (short dash), and 4 nm pore at point P (dot dash).

The electronic conductance as a function of the Fermi energy of charge carriers is shown in FIG. 3. The conductance at a particular Fermi energy is the average of the transmission probability around that carrier energy weighted by the Fermi-Dirac distribution as described in equation (4). FIG. 3a demonstrates that the conductance of the 5-GNR as a function of carrier energy is strongly dependent on nanopore size and position. As expected, the pristine 5-GNR has the largest conductance and increases relatively monotonically over a wide range of carrier energies. Compared to the pristine 5-GNR, the conductance curve of the 2 nm pore at P is much lower over the range of Fermi energies up to 0.3 eV, while the curve with the pore at Q is at least one order of magnitude higher, exhibiting a plateau beyond 0.15 eV. The 4 nm pore in the 5-GNR displays the lowest conductance values compared to all other 5-GNRs (pristine, 2 nm hole at P, 2 nm hole at Q) because of its suppressed transmission probability as discussed earlier (FIG. 2). FIG. 3b shows the conductance curves for the 15-GNR geometries. All four systems (15-GNR: pristine, 2 nm hole at P, 2 nm hole at Q, 4 nm hole at P) show a relatively monotonic increase in conductance with Fermi energy. All conductance curves achieve values about three times larger than seen for the 5-GNR, exhibiting the expected scaling with GNR width. The positional effects are mitigated as the 2 nm Q and P curves are almost identical. However, the pore size effects are retained, illustrated by a decrease in the conductance with increased (4 nm) pore size.

FIG. 3c shows the conductance properties of the 8-QPC systems. The conductance changes at varying rates throughout a range of Fermi energies. The introduction of a 2 nm pore at either P or Q enhances the magnitude of the conductance dramatically compared to that of the pristine 8-QPC, contradicting an intuitive notion that the pore acts as a scattering barrier. This behavior can be attributed to the rich interaction of the electronic states with the edge and pore boundaries as seen in FIG. 2c. Also, detected is the appearance of a NDTC region in the conductance in the case of the 8-QPC with a 4 nm hole, a feature unobserved for the GNR systems. Apparently, tailoring the pore properties within a QPC geometry can result in large changes in the conductance behavior.

FIG. 3d shows the conductance properties of the four 15-QPC systems investigated. Comparison with the 8-QPC results shows that the increased width renders the conductance less sensitive to pore geometry; in particular, NDTC regions are not recognized in the 15-QPC with a 4 nm pore. However, conductance values at Fermi energies above 0.15 eV differ greatly for different pore sizes. Paradoxically, it is observed that the conductance at low Fermi energies of the 15-QPC with a 4 nm pore is larger than in the case of the 15-QPC with a 2 nm pore at P. This behavior is due to enhanced transmission probability at low Fermi energies, caused by the particular shape of 4 nm nanopore.

Most of the conductance curves in the four panels of FIG. 3 exhibit different regions of high and low "sensitivity," which the subject disclosure defines as the slope of the conductance with Fermi energy. As a result, small changes in the Fermi energy can result in large variations in conductance similar to the transconductance in a field-effect transistor (FET).[33] Because the local carrier potential energy will be influenced by a nearby charge, which can translate into Fermi energy changes, deviations in such a charge's position can significantly modify the device conductance. This behavior can be exploited to build an ultra-sensitive charge sensing device.

Figure 4:
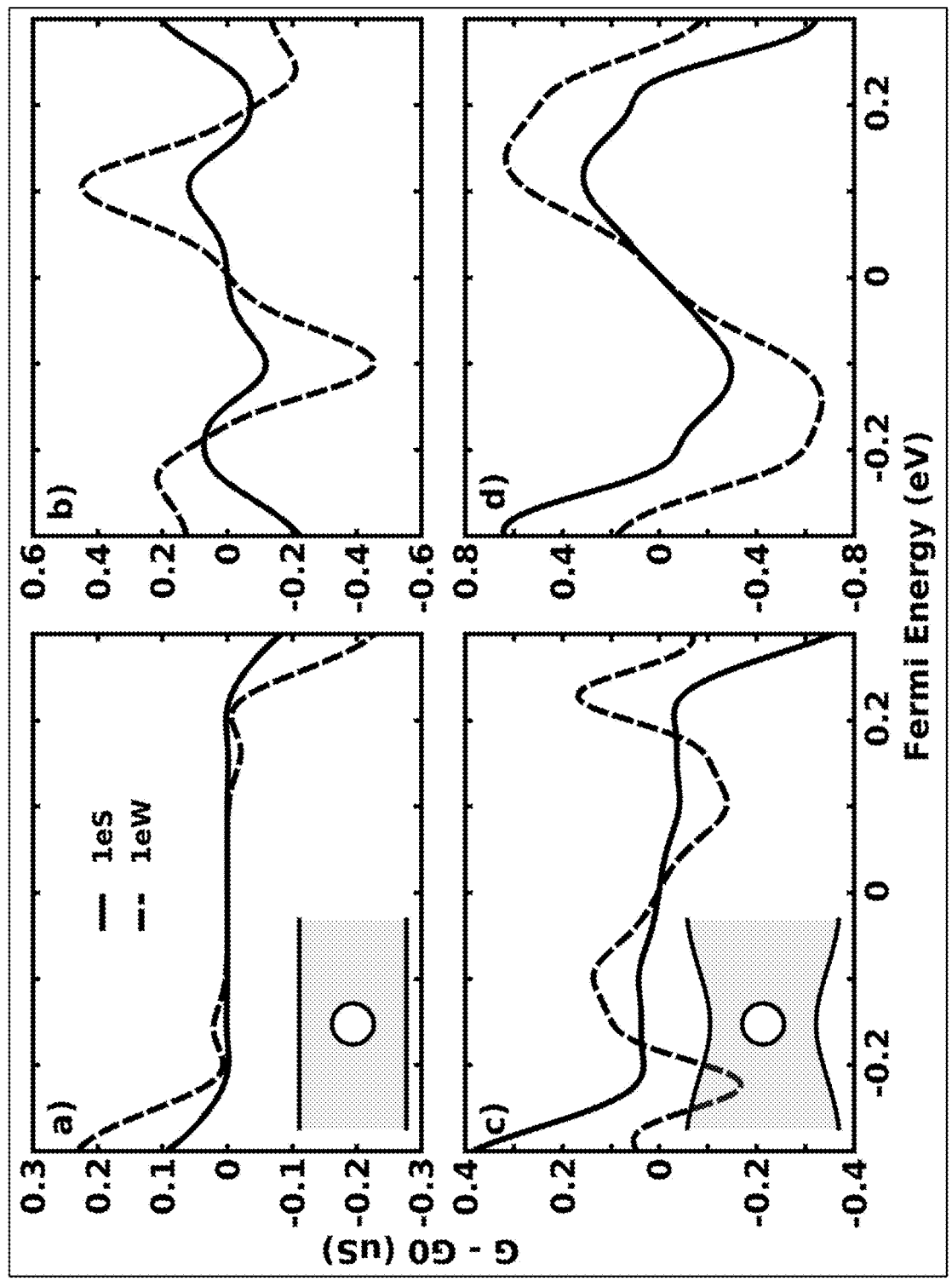
FIG. 4: Change in the conductance due to adding an external charge within the 2 nm pore. 'S' means the charge is placed one half radius south of the center of the pore, and 'W' means the charge is placed one half radius west of the center of the pore. a) 5-GNR, b) 15-GNR, c) 8-QPC and d) 23-QPC.

The influence of a solvent is treated as a mean-field approximation based on Boltzmann-statistics in the electrolyte to determine the on-site potentials on graphene as described in the methods section. Electrochemical interactions are ignored between graphene and solution, since in practice the graphene will be capped by an insulator, preventing, for the most part, direct interaction between graphene and the solvent. The effect of a test charge, placed within a pore, on electronic transport in graphene is illustrated in FIG. 4. Shown are the conductance changes upon placing a single electron charge (e) at two positions within a 2 nm pore at P; one position is at ½ radius to the west of the pore center (W or west) and the other at ½ radius south of the pore center (S or south). FIGS. 4a and 4b display the conductance response for the 5-GNR and 15-GNR respectively, while FIGS. 4c and 4d display conductance responses for the 8-QPC and 23-QPC, respectively. The difference in conductance upon charge placement varies between 0 and 0.8 µS for all geometries, which is well within the sensing range of most current probes. Conductance change for the 5-GNR (FIG. 4a) are negligible over most of the energy range for both angular charge (W & S) positions, due to the suppressed transmission probability at low carrier energies (blue curve of FIG. 2a); For the 15-GNR, 8-QPC, and 23-QPC cases (FIGS. 4b, 4c, and 4d) the angular position of the charge within the pore has a significant effect on the conductance, causing not only large differences in conductance over the investigated energy range but also a different sensitivity of the conductance to the Fermi energy. In these cases, the maximum difference in conductance occurs for a test charge in the west (south) position at smaller (larger) Fermi energies. The conductance can be either enhanced or reduced by the test charge, depending on the value of the Fermi energy. In the case of the 15-GNR (FIG. 4b), for example, when the Fermi energy lies between 0 and 0.18 eV, the conductance change for the electron test charge in the west position is positive, while the change is negative for Fermi energies above this range. Similar behavior is seen for the 8-QPC and 23-QPC, but over different Fermi energy ranges (FIGS. 4c and 4d).

It is observed that in FIG. 4, for all cases, the differences in conductance are anti-symmetric with respect to the Fermi energy. This is a direct consequence of the symmetry between electrons and holes in graphene. Because of this symmetry, electrons and holes tend to react to the same potential with opposite sign, such that the conductance changes are an odd function of Fermi energy. For instance, in FIG. 4b, there is a peak in the conductance change for the 15-GNR around 0.1 eV for all four charge configurations; a similarly shaped peak, but with opposite sign, is located at −0.1 eV. Similarly, one finds for the 23-QPC, as shown in FIG. 4d, peaks at 0.15 eV and opposite peaks at −0.15 eV. The different parity between the differential conductance curves at low energy in FIGS. 4c and 4d can be observed, which are negative for the 8-QPC (FIG. 4c) and positive for the 23-QPC (FIG. 4d). Similar conductance curves for a reduced electron charge are described below that display the same behavior as the full electron test charge but scaled by a constant factor as expected.

Figure 5:
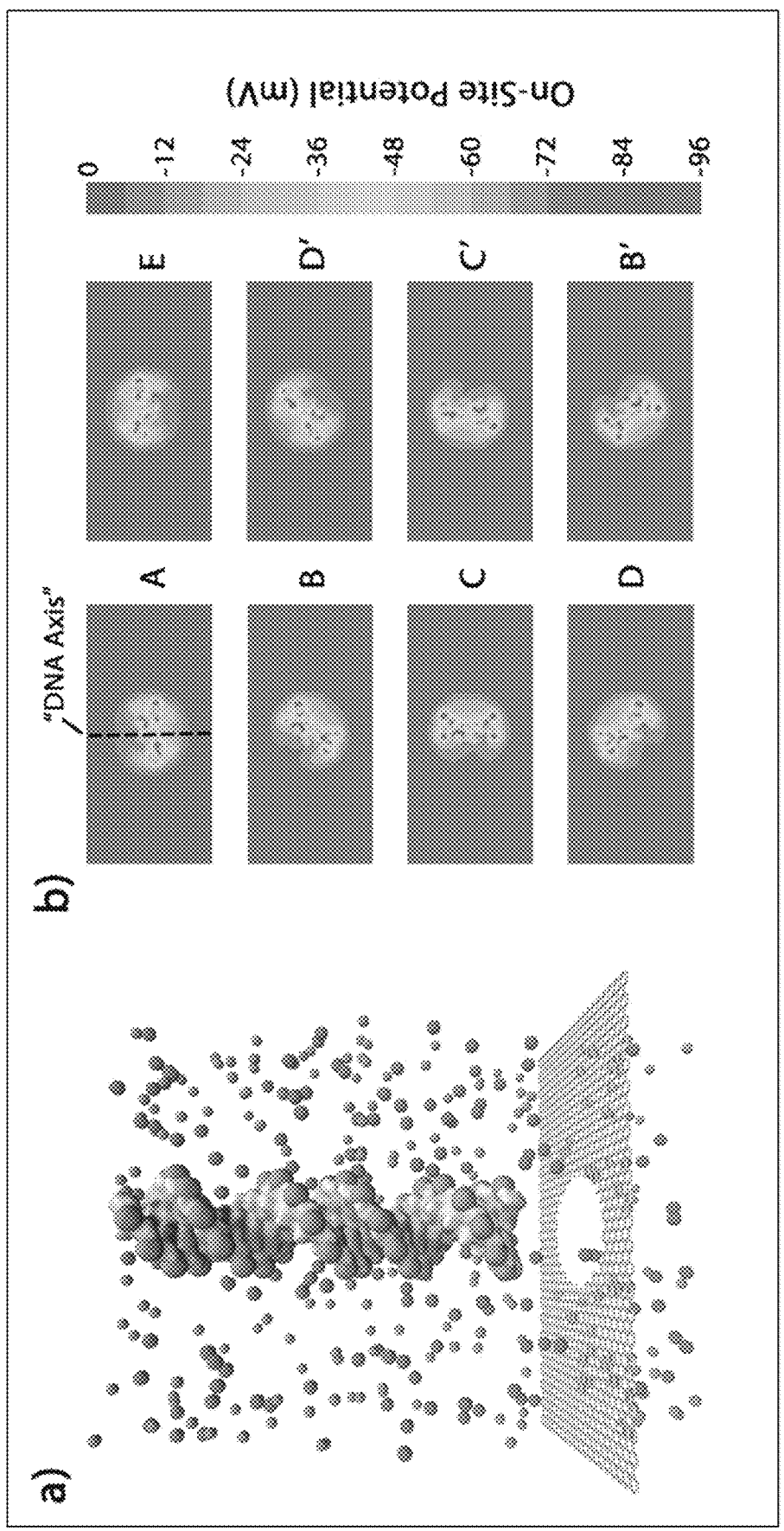
FIG. 5: a) Schematic of an AT DNA strand translocating through a pore. b) Potential maps in the graphene plane due to the DNA molecule at eight successive snapshots throughout one full rotation of the DNA strand.

In order to demonstrate a potential application of a charge-sensing device exploiting the sensitivity of geometrically-tuned GNRs, the translocation of a strand of DNA through a 2.4 nm pore located at the center (point P above) of the four edge geometries is simulated. A 24 base-pair B-type double-stranded DNA segment consisting of only AT nucleotide base-pairs is translocated. The DNA is initially placed such that the bottom of the strand is 3.5 Å above the graphene membrane, and the axis of the DNA passes through the center of the nanopore (FIG. 5a). The DNA is then rigidly translocated through the nanopore at a rate of 0.25 Å per time step (snapshot) until the DNA has passed through the pore completely. After the last ($400^{th}$) snapshot the top of the DNA strand is 13.5 Å below the graphene membrane. The charge distribution from the DNA at each time step (snapshot) is mapped into the Poisson solver, and the electric potential on the graphene membrane is calculated for each snapshot as the DNA rigidly translocates through the pore.

Due to strong screening from ions and water near the graphene membrane, the on-site electric potential of the nanopore is dominated by charges contained within a slice coplanar with the graphene membrane and directly inside the nanopore. Hence, during the translocation of the biomolecule through the nanopore, the graphene membrane will sense a succession of DNA slices, which appear as an in-place rotation of the double helix in the absence of translocation. Since it is only the charges in the pore that matter (due to the strong screening effects), the electric potentials around the pore due to the DNA being pulled through are virtually identical to the potential arising if the DNA slice coplanar with the membrane was rotated without translocation. FIG. 5b shows the on-site potentials for eight successive positions of the DNA (A-B-C-D-E-D'-C'-B') in the graphene plane, representing one half cycle of this pseudo-rotational behavior.

As mentioned above, the lattice including a nanopore may not be both x-axis and y-axis reflection symmetric with the pore at the center due to the discrete nature of the lattice. For example, the 15-GNR with a 2.4 nm pore exhibits y-axis (FIG. 2a inset) reflection symmetry, but not x-axis (FIG. 2a inset) reflection symmetry, as in the shape of the letter "Y." In contrast, the 5-GNR, 8-QPC, and 23-QPC geometries with a 2.4 nm pore exhibit both y-axis and x-axis reflection symmetry, as in the shape of the letter "X." These symmetries have an effect on the electronic conductance in GNRs when the DNA strand is introduced. When calculating the conductance from the transmission probability, it is important to note that the transmission probability itself does not represent a particular direction of current flow. In other words, a reflection about either the x- or y-axis of the lattice and its on-site electric potential map leaves the transmission probability, and hence the conductance, unchanged. When the DNA strand is translocated, the electric potential maps of successive snapshots look like A→B→C→D in FIG. 5b corresponding to the translocation of one half pitch of the DNA helix, and for the second half of the cycle the successive snapshots look like E→D'→C'→B'. The D', C', and B' potential maps are effectively the mirror images (y-axis reflected) of D, C, and B, respectively. As a result, assuming the DNA potential is reflection symmetric about its own axis ("DNA axis"), the conductance curves corresponding to geometries with only y-axis reflection symmetry should display a half-cycle "mirror" effect, repeating only after a full A→E→A rotation, i.e. the conductance should be identical for snapshots D and D', C and C', etc. On the other hand, because the electric potential maps B and D (and therefore B' and D') are identical after an x-axis reflection, the conductance should mirror after a quarter-cycle translation of the DNA and should repeat itself after a half-cycle (A→B→C→D) in the 5-GNR, 8-QPC, and 23-QPC.

Figure 6:
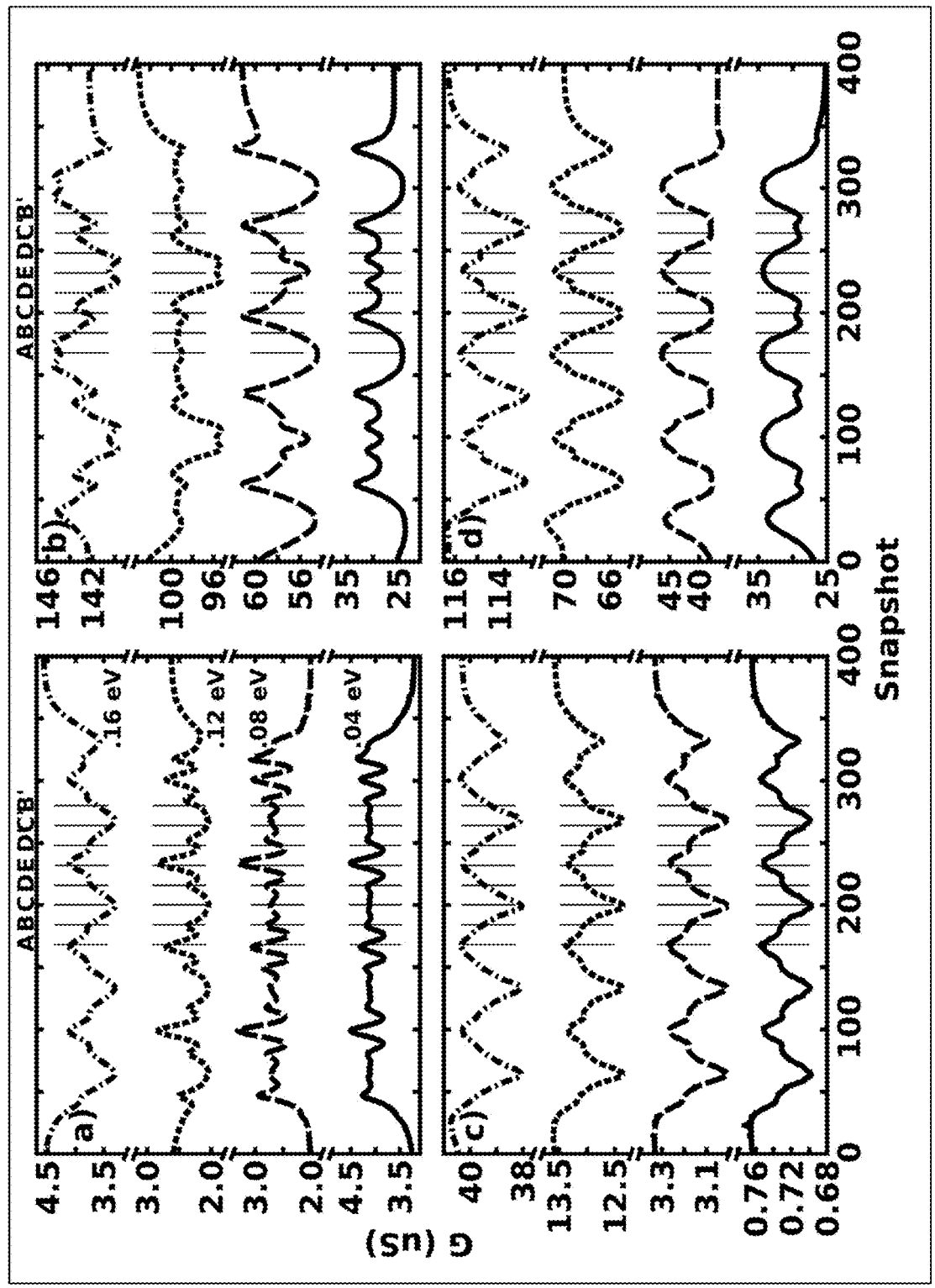
FIG. 6: Conductance as a function of DNA position (snapshot) for multiple Fermi energies, 0.04 eV (solid), 0.08 eV (long dash), 0.12 eV (short dash), and 0.16 eV (dot dash), as the DNA strand rigidly translocates through a 2.4 nm nanopore pore located at the device center (point P). a) 5-GNR, b) 15-GNR, c) 8-QPC and d) 23-QPC.

FIGS. 6a-d show the conductance as a function of the snapshot number (time) for Fermi energies 0.04 eV, 0.08 eV, 0.12 eV, and 0.16 eV above the Dirac point for each of the four geometries with a 2.4 nm pore at point P. The lines marked A-B-C-D-E-D'-C'-B' correspond to the eight potential maps in FIG. 5b, representing the translation of one full helix of the DNA. As can be seen in FIG. 6b, the 15-GNR displays the half-cycle mirroring behavior described above, only repeating after each full helix translocates through the pore. On the other hand, the 5-GNR, 8-QPC, and 23-QPC conductances shown in FIGS. 6a, 6c, and 6d respectively, display the quarter-cycle mirror effect; lines A-C represent one quarter of the helix, C-E represent the second quarter, etc. The DNA molecule in FIG. 5a, contains 24 AT base pairs, which give rise to 2.5 full turns of the double-helix. As a result, full translocation of the DNA molecule should result in 2.5 periods in the conductance curves of the 15-GNR, and 5 periods in the case of 5-GNR, 8-QPC and 23-QPC which is indeed the case as shown in FIG. 6. In these latter conductance curves, the peaks of each cycle correspond to potential map A, when the DNA axis is parallel to the y-axis, while the troughs correspond to potential map C, when the DNA axis is parallel to the x-axis. The DNA molecule is not perfectly symmetric, as the bases in a base-pair are different nucleotides; additionally, there may be a small discretization asymmetry in the potential map of the DNA. The cumulative effect is a slight difference in the conductance after a y-axis reflection, which can be recognized in FIGS. 6a, 6c, and 6d.

The large conductance variations accompanying DNA translocation through the pore demonstrate the high sensitivity of the device to external charges and their conformation. With a source-drain bias of 5 mV, the conductance (current) displays maximum variations of 0.8 to 8 µS (4 to 40 nA) depending on the particular geometry (FIG. 6), well detectable with present technology. These large variations reinforce the idea that angular position and Fermi level, in concert with each other, can strongly change the magnitude of the electrical sensitivity of the devices. Additionally, for some geometries, such as the 8-QPC (FIG. 6c), a small change in Fermi energy (0.12 eV to 0.16 eV) results in a threefold change in the magnitude of the conductance (13 µS to 40 µS) and a threefold increase in the magnitude of conductance variations (0.9 µS to 2.8 µS). Interestingly, because of the presence of NDTC regions within the investigated Fermi energy range, an increase of Fermi energy may actually decrease the conductance, as in case of the 5-GNR (FIG. 6a). Studies on electrochemical activity at the edge of graphene nanopore have been reported recently,[34] which can lead to an electrochemical sheet current in graphene of the order of 0.5 nA for a pore diameter of 2.4 nm. Although this is a large electrochemical current, the sensitivity reported here to DNA translocation is much larger than the electrochemical current measured, especially at larger Fermi energies.

Based on a simulation, a new nucleotide is within the plane of the nanopore after ~13 time steps. However, no such periodic modulation is visible in the conductance curves of FIG. 6. The reason for this is the strong screening due to the phosphate backbone on the DNA strand. As a result, the conductance variation reflects the positional changes of the backbone charges as opposed to the movement of the nucleotide charges themselves. In order to sequence DNA, one must be able to detect these nucleotides, either by translocating a single strand of DNA to prevent screening of the nucleotides by the backbone, or by making the DNA and its backbone undergo nucleotide-specific conformational changes, a topic which we are currently investigating as well as the influence of the thermal fluctuations of the DNA molecule on the g-FET conductance.

Figure 7:
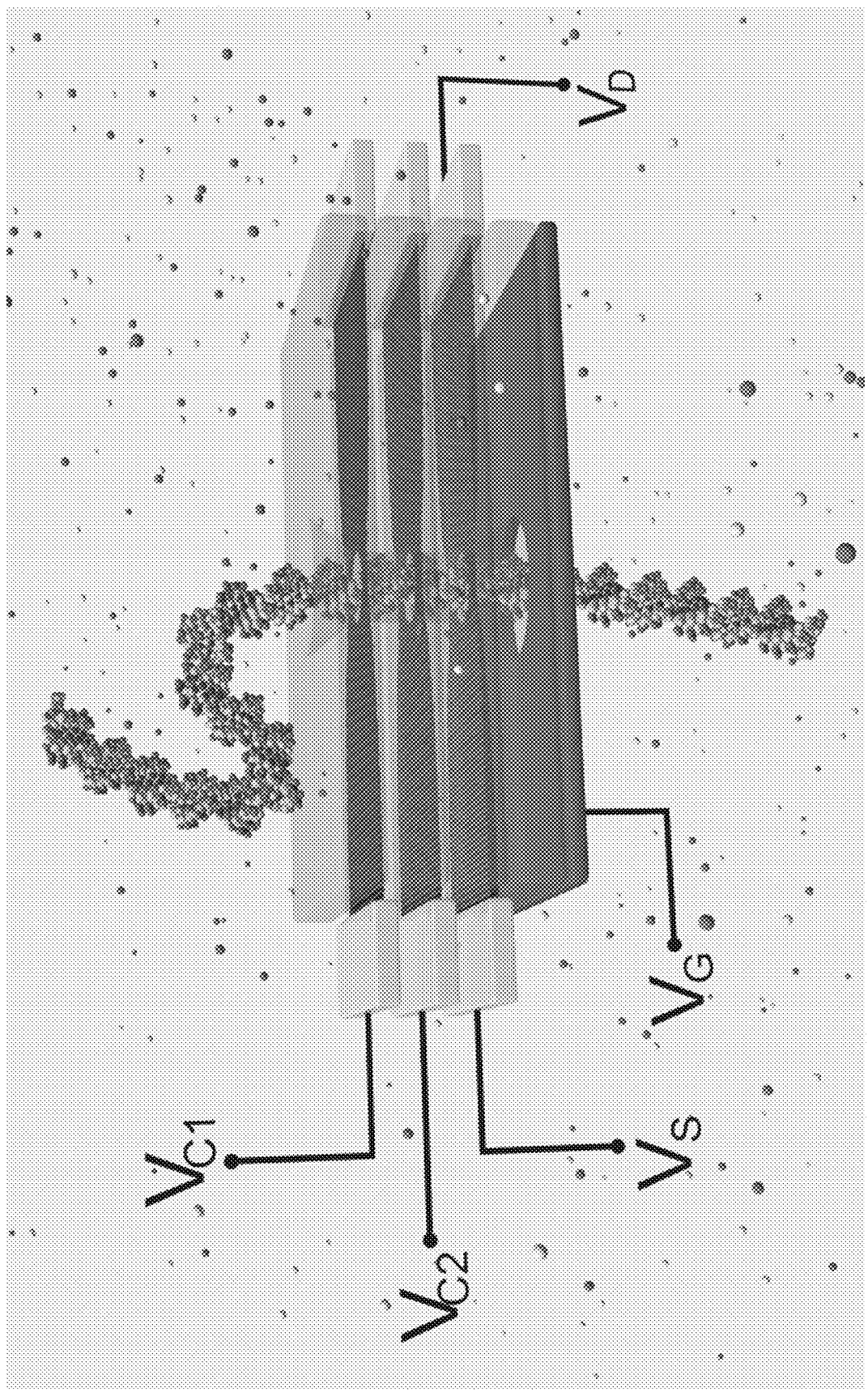
FIG. 7: Schematic diagram of a 4 layer device containing a two graphene layers (black) to control the translational motion of DNA through the nanopore. The top graphene layer ($V_{C1}$) controls the translational speed of the DNA, while the second ($V_{C2}$) controls the lateral confinement of the DNA within the nanopore. The third graphene layer ($V_{DS}$) measures the sheet current. Finally, a heavily-doped back gate (green) lies underneath the sheet current layer to control the carrier concentration. Oxide barriers (transparent) between different graphene layers provide electrical isolation. (See FIG. 13 for a cross-sectional schematic diagram).

The subject disclosure describes a strategy for sensing the molecular structure of bio-molecules by using a nanopore in electrically active mono-layer graphene shaped with a lateral constriction or QPC, employing an electrically tunable conductance to optimize detection sensitivity. The suggested measurement has been analyzed by using a self-consistent model that integrates the NEGF formalism for calculating electronic transport in the g-QPC with a detailed description of the electrical potential due to solvent, ions, and molecular charges in the nanopore. In particular, we have demonstrated that graphene QPCs are capable of detecting DNA molecules translocating through the nanopore, with a sensitivity controlled by the graphene carrier concentration. In order to achieve QPC carrier tunability, the subject disclosure describes a solid-state membrane design made of a graphene QPC sandwiched between two dielectrics to isolate the active g-layer from the electrolyte as well as suppress mechanical fluctuations of the membrane itself; the design permits simultaneous control of the carrier concentration by an external gate. The electrically active multi-layer membrane device furnishes a starting design for enhanced performance and multi-functional membranes that use more than one layer of graphene sandwiched between dielectrics or active semiconducting or metallic regions to simultaneously control and record signature of DNA passing through the nanopore (FIG. 7). Controlling the motion and translocation velocity of DNA is a currently a impediment to sequencing DNA using nanopores. One can envision that to slow down DNA translocation a bias voltage ($V_{C1}$) can be applied on one of the multiple graphene layers, which would then operate as a control gate to trap the DNA inside the pore as shown in FIG. 7. Another graphene layer ($V_{C2}$) could be used to generate a focusing field to trap the DNA and thus could help in reducing flossing of the DNA inside the pore. Finally, a third graphene layer ($V_{DS}$) could be employed to read sheet currents and discern passing nucleotides.

The electrostatic potential $\varphi(r)$ due to external charge carried by DNA is modeled as the solution of the self-consistent classical Poisson equation.

$$\nabla \cdot [\varepsilon(r)\nabla\varphi(r)] = -e[K^+(r,\varphi) - Cl^-(r,\varphi)] - \rho_{test}(r) \quad (1)$$

Here, $\varepsilon$ is the local permittivity. The RHS charge term comprises of ions in solution ($K^+$, $Cl^-$), test charges, or DNA charges and is written accordingly. The ion distributions obey Boltzmann statistics, namely[7]

$$K^+(r,\varphi) = c_0 \exp(-e\varphi/k_B T), Cl^-(r,\varphi) = c_0 \exp(e\varphi/k_B T) \quad (2)$$

Here, $K^+$ and $Cl^-$ are the local ion concentrations, e is the electronic charge, and $c_0$ is the molar concentration of KCl, which we have set to 1 M. Equation (1) is solved numerically as explained in the Supporting Information.

In order to model electronic transport sensitivity through a constriction in a g-QPC, the electronic properties of the patterned graphene layer through the tight-binding Hamiltonian are described (see also subject disclosure below)

$$H = \Sigma_{<i,j>} t_{ij} b_j^\dagger a_i + h.c. + \Sigma_i V_i c_i^\dagger c_i \qquad (3)$$

Any charge configuration present in the nanopore modifies the on-site potentials in graphene, changing the Hamiltonian (3) and thereby the transmission probability (see Supporting Information). The conductance at the Fermi energy $E_F$ in the g-QPC can be calculated as $$G(E_F) = \frac{2e}{V_b h} \int_{-\infty}^{\infty} T(E)[f(E) - f(E + eV_b)] \qquad (4)$$

where, $f(E) = [\exp((E-E_F)/k_B T) + 1]^{-1}$ is the Fermi-Dirac distribution. The carrier concentration n is controlled by the external gate bias $V_G$, i.e. en=$C_D(V_G-V_T)$ where $C_D$ is the dielectric capacitance and $V_T$ is the threshold voltage for electron or hole conduction in the QPC. Since $E_F=E_F(n)$, the carrier concentration and the Fermi energy can be interchangeable, even though the Fermi energy is the relevant parameter. A source-drain bias ($V_b$) of 5 mV and a system temperature of 300 K can be assumed. Conductance may be reduced by non-ideal boundaries of the QPC. However, the main conclusions pertain to the response of the conductance to changes in the overall geometry and carrier concentration, and they are expected to remain valid if the conductance is significantly reduced, even by an order of magnitude.

By using the Non-Equilibrium Green's Function technique the subject disclosure shows that the shape of the edge, the carrier concentration, and the position and size of a nanopore in graphene nanoribbons can strongly affect its electronic conductance as well as its sensitivity to external charges. This technique, combined with a self-consistent Poisson-Boltzmann formalism to account for ion charge screening in solution, is able to detect the rotational and positional conformation of a DNA strand inside the nanopore. The subject disclosure shows that a graphene membrane with quantum point contact (QPC) geometry exhibits greater electrical sensitivity than a uniform armchair geometry provided that the carrier concentration is tuned to enhance charge detection. The subject disclosure generally describes a membrane design that contains an electrical gate for a graphene-based DNA sensing device.

Rapidly sequencing the human genome in a cost-effective manner can revolutionize modern medicine. This subject describes a new paradigm for sensing DNA molecules by threading them through an electrically active solid-state nanopore device containing a constricted graphene layer. The subject disclosure shows that the electrical sensitivity of the graphene layer can be easily tuned by both shaping its geometry and modulating its conductance by means of an electric gate integrated in the membrane.

The tight-binding graphene Hamiltonian is given by $$H = \sum_{\langle i,j \rangle} t_{ij} b_j^\dagger a_i + h.c. \qquad (S5)$$

where $t_{ij}$ is the site-dependent hopping parameter and $b_j^\dagger a_i$ represents an electron hopping from an A sublattice site i to a nearest-neighbor B sublattice site j. After transforming this to a momentum-space representation and solving for the band structure, we notice that the Fermi energy of the system lies at two non-equivalent points in the first Brillouin zone designated K and K', respectively. After expanding around these two points, for low energies, we obtain the Dirac equation and the corresponding full wavefunction Ψ for each sublattice.

$$H_q = \mp i\hbar v_F \sigma \cdot q \qquad (S6)$$

$$\Psi_{q,A/B}(r) = e^{iK\cdot r}\psi_{q,A/B}(r) + e^{iK'\cdot r}\psi'_{q,A/B}(r) \qquad (S7)$$

Here, $\mp$ refers to the K,K' points respectively (known as the two Dirac points), and ψ,ψ' are the eigenspinors corresponding to the K,K' Hamiltonians. To study graphene nanoribbons (GNRs), we assume both translational invariance and that the total wavefunction goes to zero at the boundaries on each sublattice independently. Because the each component of the total wavefunction needs to be zero at the boundary simultaneously, the relationship between components can become quite complicated, especially when considering a non-uniform GNR edge.[2] This will result in a very nonlinear and complex transmission function when compared to the uniform GNR case (FIG. 2).

A tight-binding Hamiltonian can be implemented as a sparse matrix M where the matrix element $M_{ij}$ represents the interaction between lattice sites i and j. The hexagonal lattice is represented as square lattice by a simple transformation, preserving the topology of the lattice. The non-equilibrium Green's function (NEGF) formalism, associated with the Hamiltonian (S1) permits one to calculate the transport properties of the g-QPC device. Including the effects of the leads, the Green's function for the full device reads $$G_D = \left[E + i\eta - H_D - \sum_p V_{pD} g_p V_{Dp}\right]^{-1} = \left[E + i\eta - H_D - \sum_p S_p\right]^{-1} \qquad (S8)$$

where $H_D$ is the device Hamiltonian without leads, $V_{pD}$ and $V_{Dp}$ are interaction potentials between the isolated device and the lead p, and $g_p$ is the Green's function of the isolated lead p. $S_p$ is the self-energy of lead p. To calculate $g_p$ of the semi-infinite lead p, we use the recursive technique described by Sancho et al. An algorithm was executed for 200 recursions, beyond what is required for convergence. The transmission probability from lead p to lead q is $$T_{pq}(E) = Tr(\Gamma_p G_D \Gamma_q G_D^\dagger) \text{ with } \Gamma_p = i(S_p - S_p^\dagger) \qquad (S9)$$

from which one can calculate the conductance. The matrix equations are solved using the sparse matrix linear solving algorithms included in a Scipy v0.11.0 package, linked against the UMFPACK v5.2 sparse matrix routines.

The non-linear Poisson equation described above is solved using a Newton-multigrid scheme. The anisotropy in the permittivity of the system requires a finite volume discretization with operator-based interpolation for the grid operators used in the multigrid scheme. The system employs a non-uniform mesh with a mesh size ranging from (Å/3 near the pore mouth and 3 Å/2 far away from the pore mouth). The maximum size of the mesh points used in the simulation was 256×512×256. The relativity permittivity of water and graphene were set to 78 and 6 respectively. The system was subject to Dirichlet conditions along the $\hat{z}$ direction, and Neumann boundary conditions are applied in $\hat{x}$ and $\hat{y}$ (FIG. 2) directions. The simulated system size varies from 10×5×20 nm³ to 10×23×20 nm³.

The initial structure of the DNA was generated using the program X3DNA and the psfgen module of VMD. The atomic coordinates and charge from the DNA were then mapped onto a 3D grid, which was used as the input charge configuration for the Poisson solver.

Figure 8:
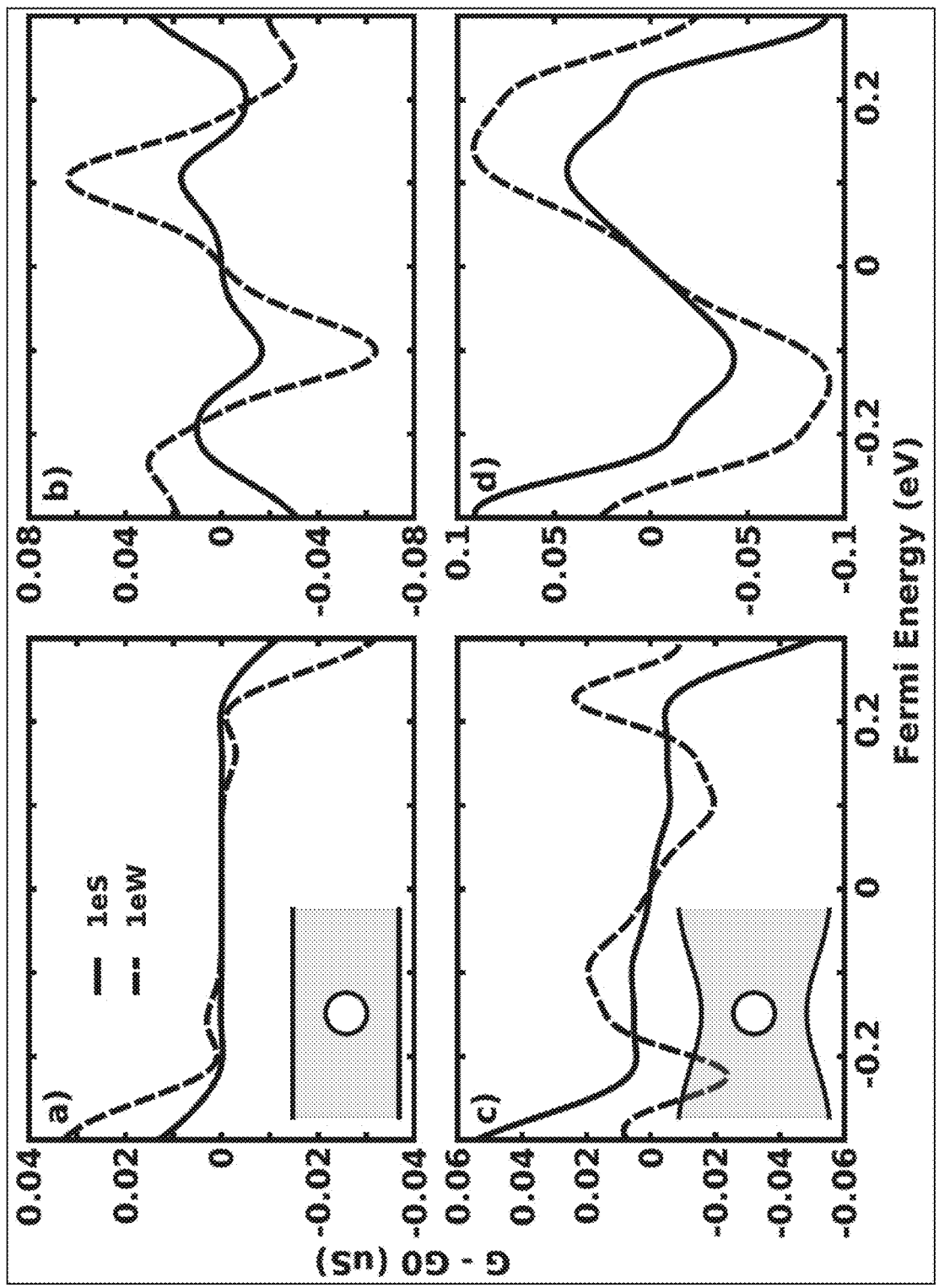
FIG. 8: Conductance variations of placing an eighth of an electron test charge in the south and west positions of a 2 nm nanopore located at point P (figure inset) in a a) 5-GNR, b) 15-GNR, c) 8-QPC, and d) 23-QPC.

FIG. 8 shows the conductance variation of placing an eighth of an electron test charge in the west and south positions of the 2 nm nanopore located at point P (FIG. 8 inset). As mentioned above, the variations follow virtually the same trend as for the full electron test charge, except for a scaling by factor ⅛, as expected due to the linear scaling of the potential with test charge magnitude.

Figure 9:
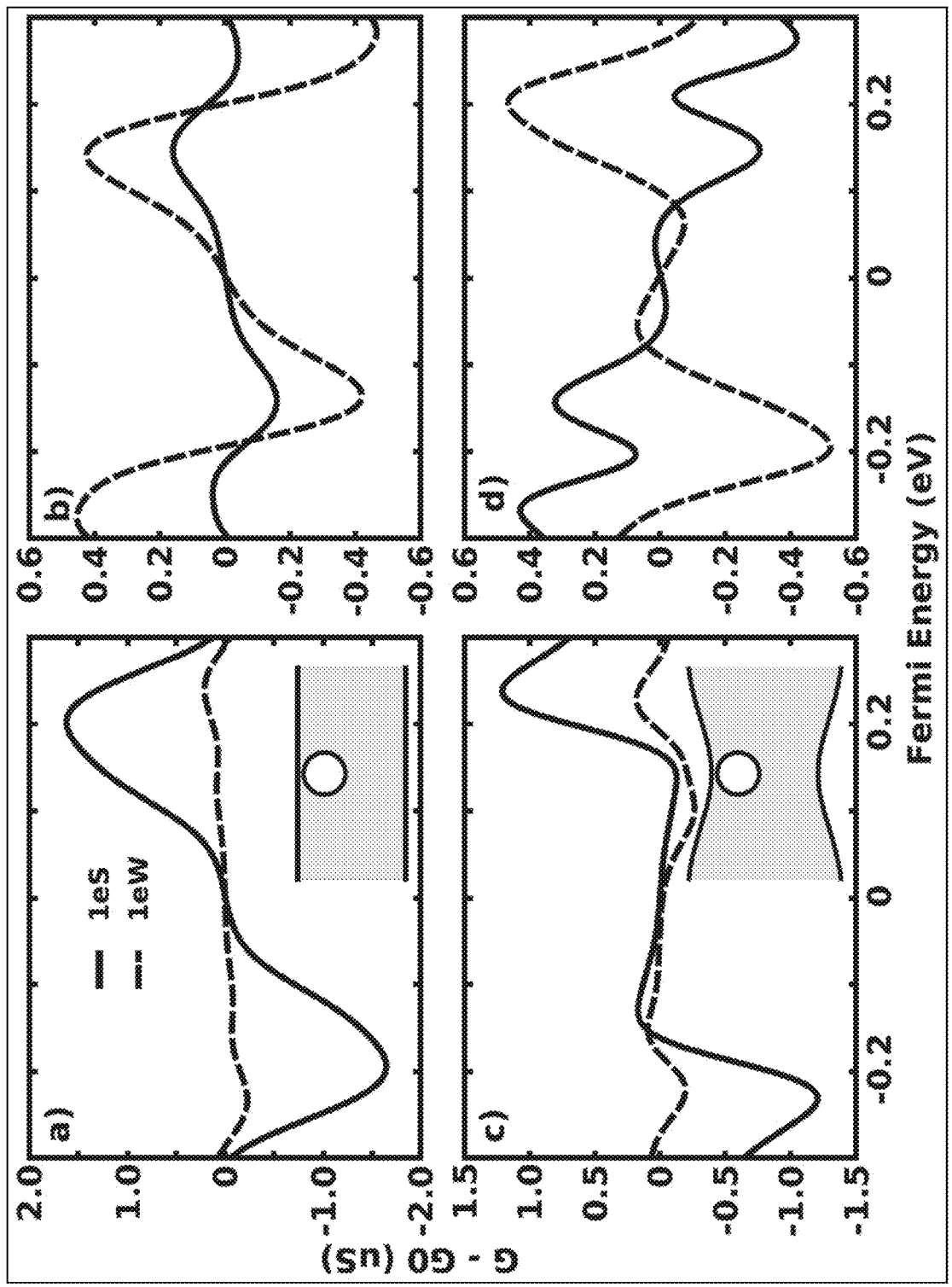
FIG. 9: Conductance variations of placing a full electron test charge in the south and west positions of a 2 nm nanopore located at point Q (figure inset) in a a) 5-GNR, b) 15-GNR, c) 8-QPC, and d) 23-QPC.

FIG. 9 shows the conductance variation of placing a full electron test charge in the west and south positions of the 2 nm nanopore located at point Q (FIG. 9 inset) of each of the four edge geometries. Similar to the case with the pore at P, the variations are strongly dependent on the position of the charge within the nanopore as well as the Fermi level. The magnitudes of the conductance variations in the 5-GNR (FIG. 9a) and 8-QPC (FIG. 9c) geometries are larger than those of the same geometries with the pore at point P. Here, for the 5-GNR, the largest variations are almost 1.7 μS for a charge placed in the south position of the pore in the 5-GNR, and are almost 1.3 μS for a charge placed in the south position of the 8-QPC pore. When the charge is placed in the west position of the pore, on the other hand, the conductance variations are much smaller, being 0.25 μS and 0.2 μS for the 5-GNR and 8-QPC, respectively. This once again demonstrates the large sensitivity of the conductance to the angular position of the charge within the nanopore.

Figure 10:
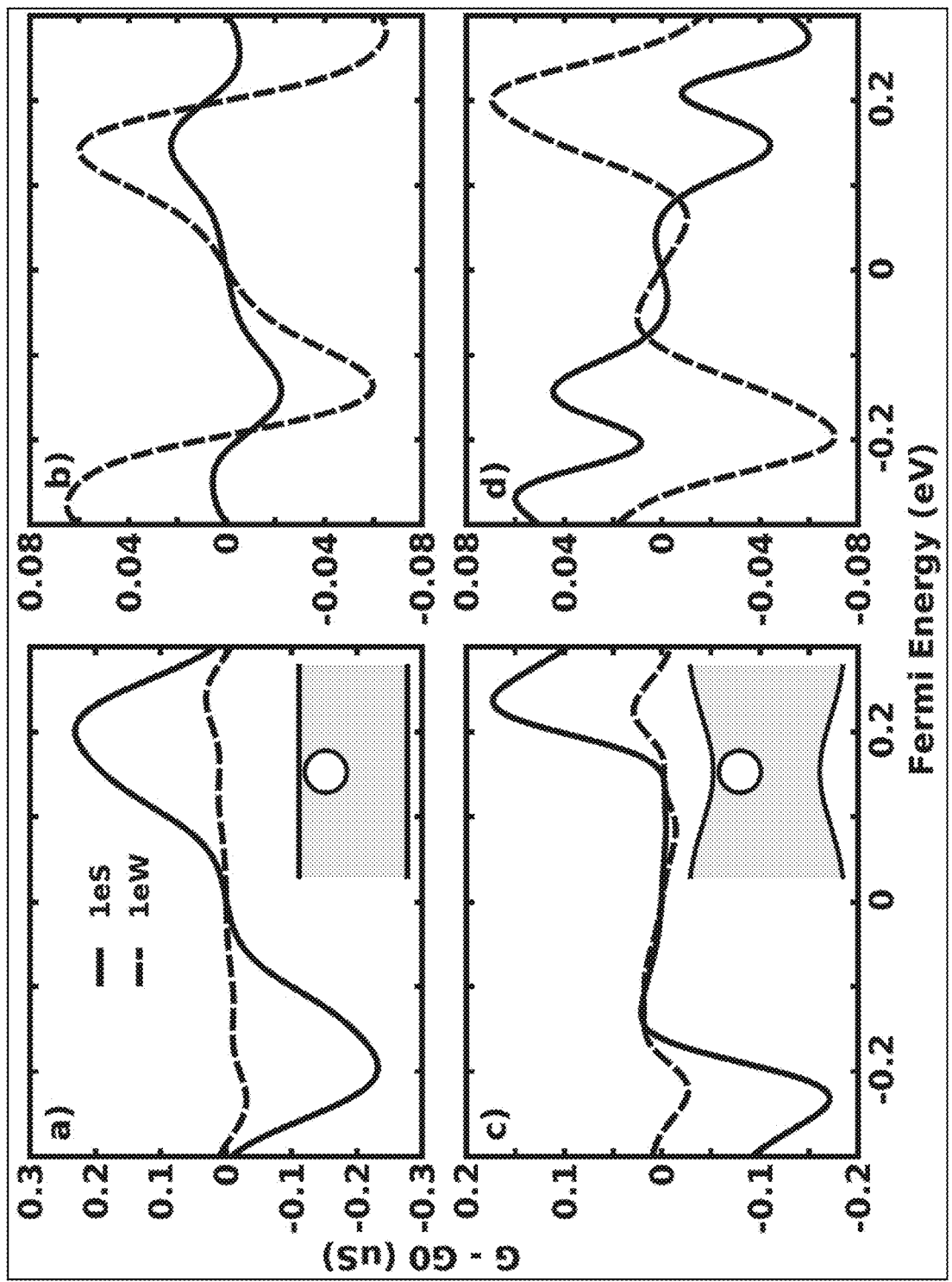
FIG. 10: Conductance variations of placing an eighth of an electron test charge in the south and west positions of a 2 nm nanopore located at point Q (figure inset) in a) 5-GNR, b) 15-GNR, c) 8-QPC, and d) 23-QPC.
Figure 11:
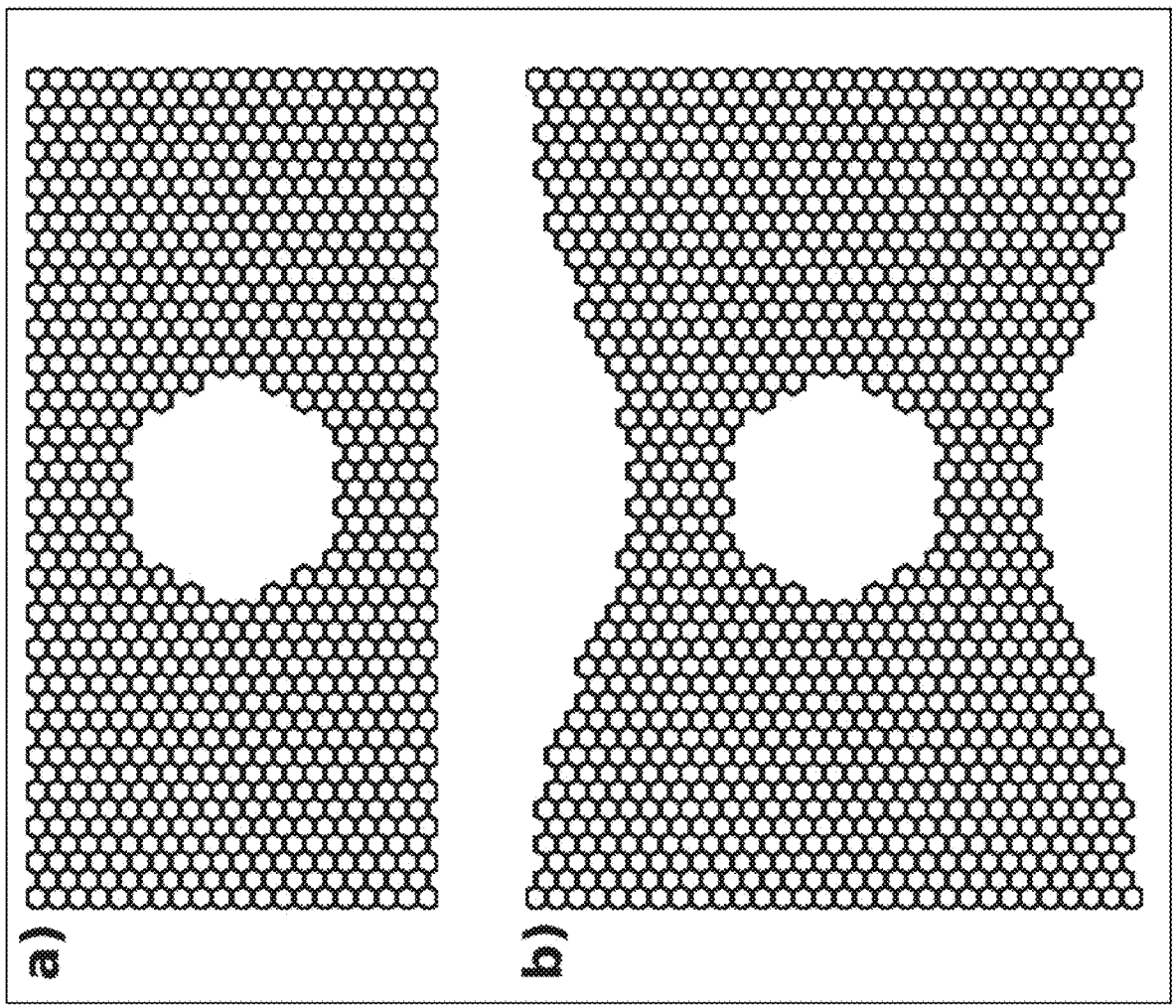
FIG. 11: Illustration depicting the precise lattice configuration used to simulate the a) 5-GNR and b) 8-QPC nanoribbons with a 2.4 nm diameter nanopore.
Figure 12:
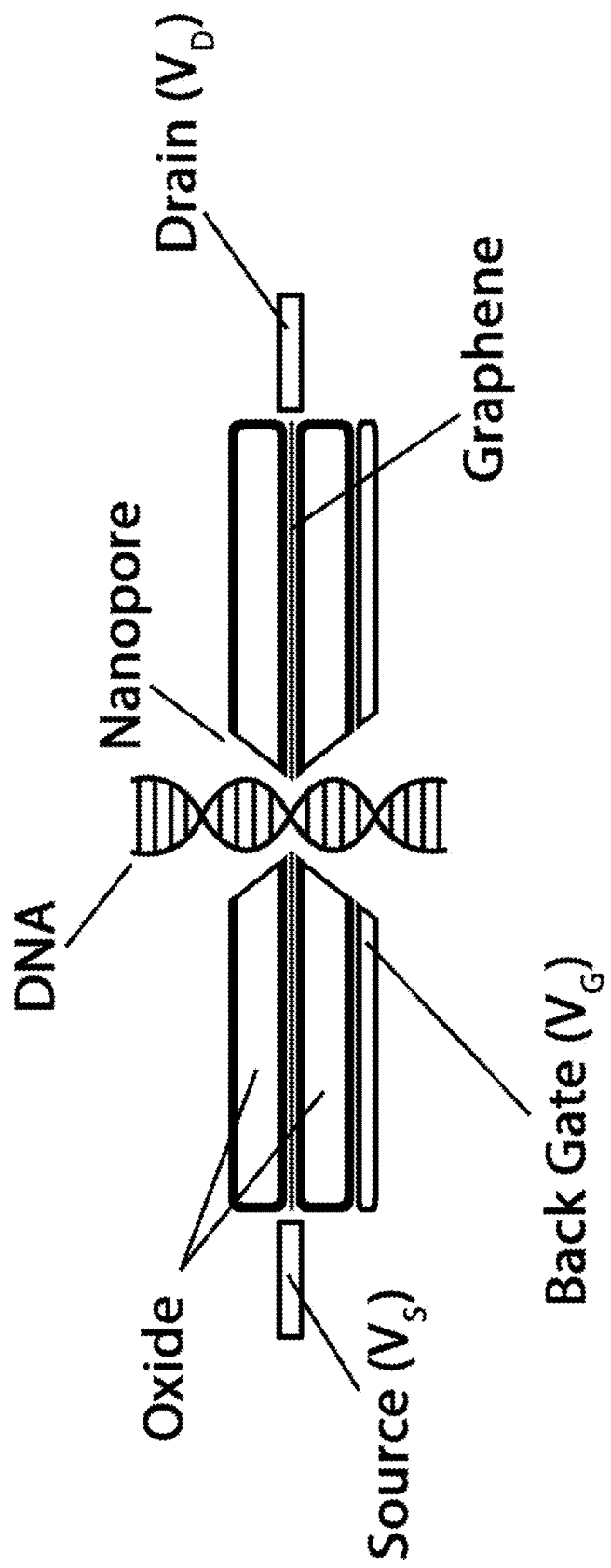
FIG. 12: Cross-sectional schematic diagram through the central axis of the nanopore of the multilayer device illustrated in FIG. 1 showing source ($V_S$) and drain ($V_D$) contacts as well as the back gate ($V_G$).
Figure 13:
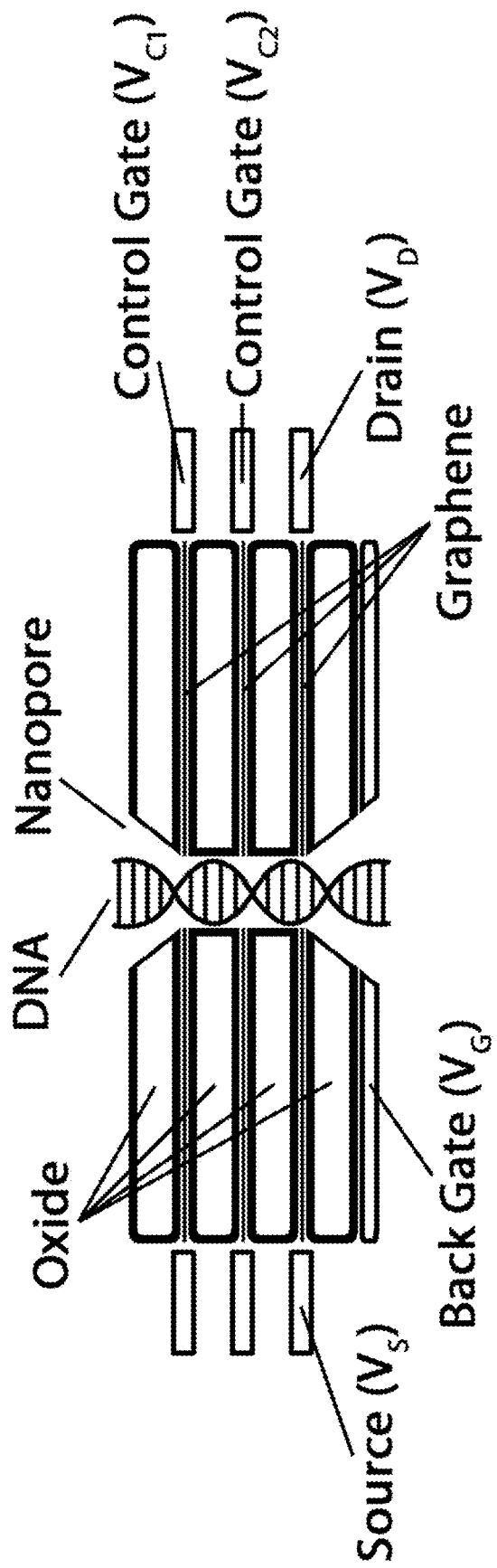
FIG. 13: Cross-sectional schematic diagram through the central axis of the nanopore of the multilayer device illustrated in FIG. 7 showing source ($V_S$), drain ($V_D$), and control ($V_{C1}$ and $V_{C2}$) contacts, as well as a back gate ($V_G$).

For the wider 15-GNR (FIG. 9b) and 23-QPC (FIG. 9d) geometries, the conductance variations are similar in magnitude for the geometries with the pore at point P. For the 15-GNR, the maximum conductance variations are 0.45 μS and 0.18 μS for a test charge placed in the west and south positions of the pore, respectively. For the 23-QPC, the largest variations are 0.5 μS and 0.45 μS for a test charge placed in the west and south positions in the pore, respectively. In all four cases, the conductance variations do not follow a strictly increasing relationship with Fermi energy, displaying many regions of negative differential resistance, sometimes of large magnitude. For example, as seen in FIG. 9b, the conductance variation drops by 0.8 μS, a factor of over 200%, when the Fermi energy is changed from 0.15 eV to 0.25 eV. As a result, the Fermi energy plays a strong role in determining the sensitivity of these devices to external electric potentials. FIG. 10 shows the conductance variations for an eighth of an electron test charge placed in a 2 nm pore at point Q (FIG. 10 inset) for all four geometries. Similarly to the other case, the charge variations are almost identical to the full electron case, scaled by a factor ⅛, as expected.

Figure 14:
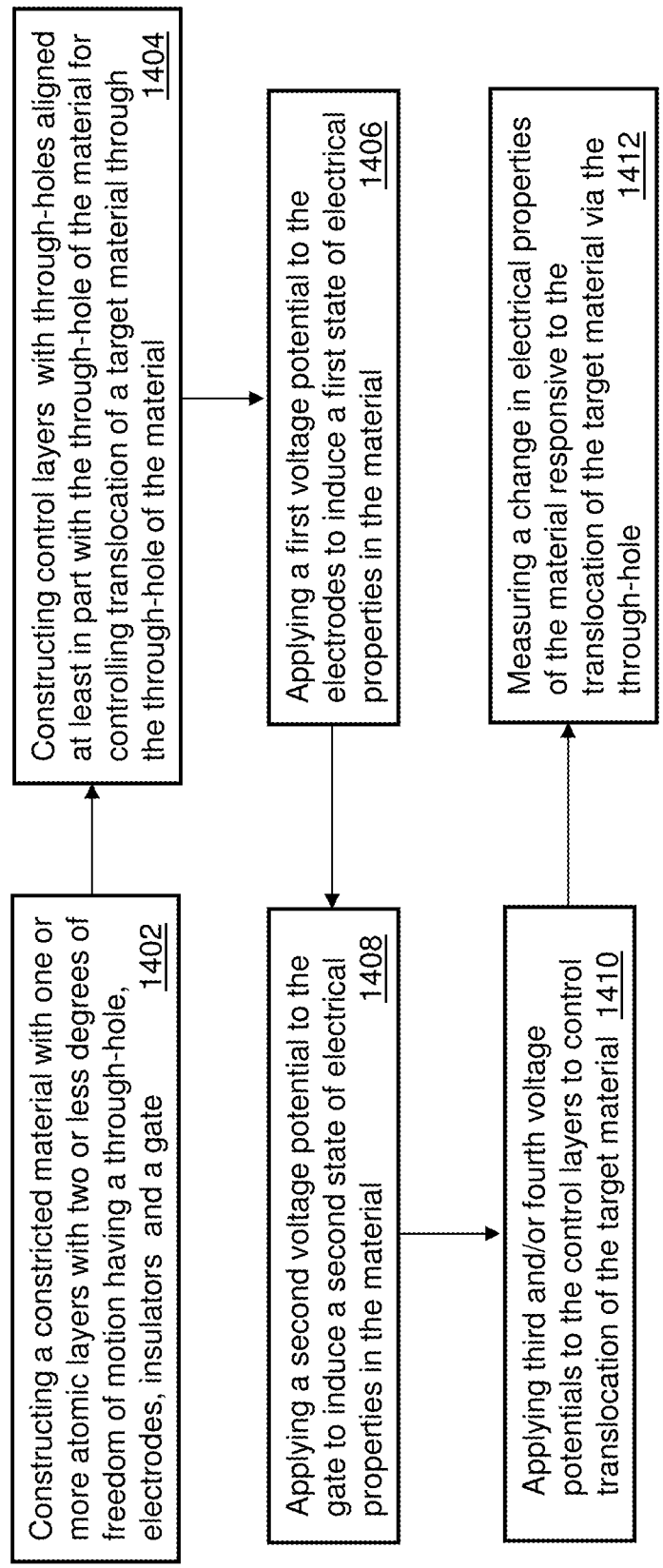
FIG. 14 depicts an illustrative method for constructing and utilizing the embodiments in the subject disclosure.

FIG. 14 depicts an illustrative method 1400 for constructing and utilizing the embodiments in the subject disclosure. Method 1400 can begin with constructing at step 1402 a constricted material having a through-hole and electrodes and insulators such as shown in FIG. 1. The material can be any material having one or more atomic layers with two or less degrees of freedom of motion of charges in the material such as, for example, grapheme, molybdenum disulfide, transition metal chalcogenides, or combinations thereof. The insulators can comprise an oxide material or dielectric material such as aluminum oxide, a hafnium oxide, a silicon dioxide, or combinations thereof, and the dielectric material can be, for example, silicon nitride. The through-hole can be a nanopore with a regular or irregular shape. The constriction can also be of a regular or irregular shape. The gate can be constructed from any material that can cause a change in carrier concentration in the material having the constriction such as, for example, a metal, a doped semiconductor, grapheme, or combinations thereof. The target material can be embedded in a liquid solution (such as an ionic solution) for assisting the translocation of the target material in the through-holes. At step 1404, control layers can be constructed in addition to the structure of described at step 1402 with through-holes aligned at least in part with the through-hole of the constricted material for controlling translocation of the target material through the through-hole of the constricted material such as shown in FIG. 7. The target material can be a biological or non-biological material, which is intended to be analyzed while traversing the through-hole of the material having the constriction.

To analyze the target material, a first voltage potential can be applied at step 1408 to the electrodes of the constricted material to induce a first state of electrical properties in the material (e.g., Vs and Vd). The state of electrical properties can include, for example, inducing conductance of charges (holes and/or electrons) in the constricted material, or inducing an electric field applied to the charges in the constricted material which may or may not result in the conduction of the charges. At step 1410, a second voltage potential can be applied to the gate (Vg) to induce a second state of electrical properties in the material. The second state can include inducing a change in charge concentration of charges in the constricted material. To control translocation of the target material, third and fourth voltage potentials (Vc1 and Vc2) can be applied to the control layers. As the target material traverses the through-hole of the constricted material, segments of the target material can in turn cause changes in the electrical properties of the constricted material. Such changes can be measured at step 1412 according to a change in voltage, current or both in the constricted material of step 1402.

From the foregoing descriptions, it would be evident to an artisan with ordinary skill in the art that the aforementioned embodiments can be modified, reduced, or enhanced without departing from the scope and spirit of the claims described below. For example, a controller (such as a microcomputer or state machine) can be used to control variable voltage sources that apply the voltage potentials described in method 1400. A sensor such as a voltmeter or ammeter can be used and controlled by the controller for measuring changes in the electrical properties of the constricted material. Other suitable modifications can be applied to the subject disclosure. Accordingly, the reader is directed to the claims for a fuller understanding of the breadth and scope of the subject disclosure.

Figure 15:
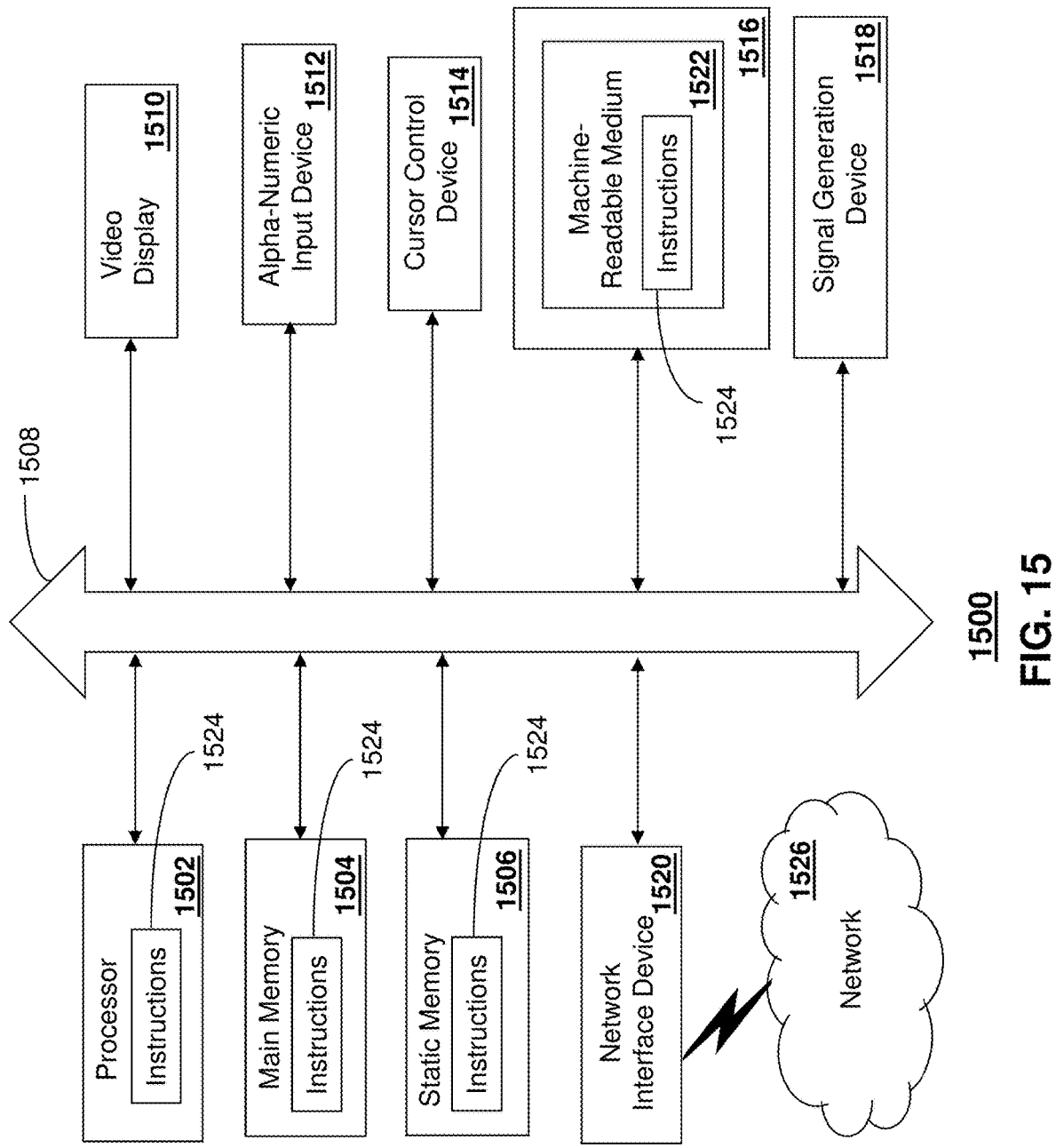
FIG. 15 depicts an illustrative diagrammatic representation of a machine in the form of a computer system within which a set of instructions, when executed, may cause the machine to perform any one or more of the methodologies disclosed herein.

FIG. 15 depicts an exemplary diagrammatic representation of a machine in the form of a computer system 1500 within which a set of instructions, when executed, may cause the machine to perform any one or more of the methods discussed above. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1500 may include a processor 1502 (e.g., a central processing unit (CPU), a graphics processing unit (GPU, or both), a main memory 1504 and a static memory 1506, which communicate with each other via a bus 1508. The computer system 1500 may further include a video display unit 1510 (e.g., a liquid crystal display (LCD), a flat panel, or a solid state display. The computer system 1500 may include an input device 1512 (e.g., a keyboard), a cursor control device 1514 (e.g., a mouse), a disk drive unit 1516, a signal generation device 1518 (e.g., a speaker or remote control) and a network interface device 1520.

The disk drive unit 1516 may include a tangible computer-readable storage medium 1522 on which is stored one or more sets of instructions (e.g., software 1524) embodying any one or more of the methods or functions described herein, including those methods illustrated above. The instructions 1524 may also reside, completely or at least partially, within the main memory 1504, the static memory 1506, and/or within the processor 1502 during execution thereof by the computer system 1500. The main memory 1504 and the processor 1502 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 622 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 1500.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A method, comprising:
   providing a material extending in a first direction and having a first end and a second end, extending in a second direction perpendicular to the first direction, and having one or more atomic layers with two or less degrees of freedom of motion of charges in the material;
   constricting the material in the second direction to generate a constriction in the material having an edge contour, thereby configuring electrical properties in the material;

coupling the first end of the material to a first electrode;
coupling the second end of the material to a second electrode, thereby forming an electrically conducting region of the material between the first electrode and the second electrode;
coupling a gate that is a separate component from the material to the material;
providing a first through-hole in the material near a vicinity of the constriction, the first through-hole being located within and substantially coplanar with the electrically conducting region, wherein the electrical properties in the material are determined at least in part by a distance between the first through-hole and the edge contour, wherein the first through-hole is located closer to the edge contour than a center of the material, and wherein the first through-hole is the only through-hole in the material;
providing a second through-hole in the gate, wherein the first through-hole and the second through-hole are substantially coaxially aligned;
applying a first voltage potential to the first electrode and to the second electrode;
applying a second voltage potential to the gate, thereby adjusting an electrical conductance and a charge concentration of the material in the electrically conducting region;
introducing a target material at one of the first through-hole or the second through-hole; and
measuring a change in electrical properties of the material responsive to the target material traversing the first through-hole of the material along a path traversing the first through-hole and the second through-hole and substantially transverse to the electrically conducting region,
wherein a response to the target material traversing the first through-hole comprises a change in the conductance of the material in the electrically conducting region.

2. The method of claim 1, further comprising applying a first insulator to a top surface of the material, and a second insulator to a bottom surface of the material, wherein the first insulator comprises a third through-hole, wherein the second insulator comprises a fourth through-hole, and wherein the first through-hole, the second through-hole, the third through-hole, and the fourth through-hole are substantially coaxially aligned.

3. The method of claim 2, wherein the first insulator and the second insulator comprise an oxide material or a dielectric material.

4. The method of claim 3, wherein the oxide material comprises one of an aluminum oxide, a hafnium oxide, a silicon dioxide, or combinations thereof, and wherein the dielectric material comprises silicon nitride.

5. The method of claim 1, wherein the material comprises graphene.

6. The method of claim 5, wherein the material comprises a quantum point contact.

7. The method of claim 1, wherein the material comprises a transition metal chalcogenide.

8. The method of claim 5, wherein a state of the electrical properties of the material is controlled by one of the first voltage potential, the second voltage potential, a first shape of the constriction, a second shape of the first through-hole, a first size of the constriction, a second size of the first through-hole, or any combination thereof, and wherein changes in the state of the electrical properties of the material are caused by the target material traversing the first through-hole of the material.

9. The method of claim 8, wherein the first through-hole comprises a nanopore.

10. The method of claim 9, wherein the nanopore has an irregular geometry.

11. The method of claim 2, wherein the first through-hole, second through-hole, third through-hole and fourth through-hole each comprises a nanopore, and wherein the third through-hole is tapered.

12. The method of claim 1, wherein the charges in the material comprise holes.

13. The method of claim 1, wherein the charges in the material comprise electrons.

14. The method of claim 1, further comprising:
at least one control layer having a third through-hole substantially coaxially aligned with the first through-hole and the second through-hole; and
applying at least a third voltage potential to the at least one control layer to control movement of the target material through the first through-hole, the second through-hole, and the third through-hole.

15. The method of claim 1, wherein the target material comprises a biological target material.

16. The method of claim 15, wherein the biological target material comprises one of a deoxyribonucleic acid, ribonucleic acid, a protein, or combinations thereof, and wherein the biological target material is combined with an ionic solution.

17. The method of claim 15, further comprising combining the target biological material with a liquid solution.

18. The method of claim 2, wherein the second insulator is between the material and the gate.

19. The method of claim 18, further comprising providing a focusing field gate comprising a fifth through-hole above the first insulator, and a third insulator above the focusing field gate comprising a sixth through-hole, and applying a third voltage potential to the focusing field gate to reduce flossing of the target material, wherein the fifth through-hole and the sixth through-hole are substantially coaxially aligned with the third through-hole.

20. The method of claim 19, further comprising providing a control gate comprising a seventh through-hole above the third insulator, and a fourth insulator above the control gate comprising an eighth through-hole, and applying a fourth voltage potential to the control gate to trap the target material, wherein the seventh through-hole and the eighth through-hole are substantially coaxially aligned with the sixth through-hole.

21. The method of claim 20, wherein the first through-hole, second through-hole, third through-hole, fourth through-hole, fifth through-hole, sixth through-hole, seventh through-hole, and eighth through-hole each comprises a nanopore, and wherein the eighth through-hole is tapered.

22. A method, comprising:
providing a material extending in a first direction and having a first end and a second end, extending in a second direction perpendicular to the first direction, and having one or more atomic layers with two or less degrees of freedom of motion of charges in the material;
constricting the material in the second direction to generate a constriction in the material having an edge contour, thereby configuring electrical properties in the material;
coupling the first end of the material to a first electrode;

coupling the second end of the material to a second electrode, thereby forming an electrically conducting region of the material between the first electrode and the second electrode;

coupling a gate that is a separate component from the material to the material, wherein the gate comprises a metal, a doped semiconductor, graphene, a transition metal chalcogenide or a combination thereof;

providing a first through-hole in the material near a vicinity of the constriction, the first through-hole being located within and substantially coplanar with the electrically conducting region, wherein the electrical properties in the material are determined at least in part by a distance between the first through-hole and the edge contour, wherein the first through-hole is located closer to the edge contour than a center of the material, and wherein the first through-hole is the only through-hole in the material;

providing a second through-hole in the gate, wherein the first through-hole and the second through-hole are substantially coaxially aligned;

applying a first voltage potential to the first electrode and to second electrode;

applying a second voltage potential to the gate, thereby adjusting an electrical conductance and a charge concentration of the material in the electrically conducting region;

introducing a target material at one of the first through-hole or the second through-hole; and measuring a change in electrical properties of the material responsive to the target material traversing the first through-hole of the material along a path substantially transverse to the electrically conducting region, wherein a response to the target material traversing the first through-hole comprises a change in a conductance of the electrically conducting region, and wherein a sensitivity of the response is determined at least in part according to the second voltage potential.

23. A method, comprising:

providing a material extending in a first direction and having a first end and a second end, extending in a second direction perpendicular to the first direction, and having one or more atomic layers with two or less degrees of freedom of motion of charges in the material;

constricting the material in the second direction to generate a constriction in the material having an edge contour, thereby configuring electrical properties in the material;

coupling the first end of the material to a first electrode;

coupling the second end of the material to a second electrode, thereby forming an electrically conducting region of the material between the first electrode and the second electrode;

coupling a gate that is a separate component from the material to the material;

providing a first through-hole in the material near a vicinity of the constriction, the first through-hole being located within and substantially coplanar with the electrically conducting region, wherein the electrical properties in the material are determined at least in part by a distance between the first through-hole and the edge contour, wherein the first through-hole is located closer to the edge contour than a center of the material, and wherein the first through-hole is the only through-hole in the material;

providing a second through-hole in the gate, wherein the first through-hole and the second through-hole are substantially coaxially aligned;

applying a first voltage potential to the first electrode and to the second electrode;

applying a second voltage potential to the gate, thereby adjusting an electrical conductance and a charge concentration of the material in the electrically conducting region;

introducing a target material at one of the first through-hole or the second through-hole; and measuring a change in electrical properties of the material in the electrically conducting region responsive to the target material traversing the first through-hole of the material along a path traversing the first through-hole and the second through-hole and substantially transverse to the electrically conducting region, wherein measuring the change in the electrical properties comprises measuring a change in current, conductance, voltage, or a combination thereof.

* * * * *